United States Patent
Bossenmaier et al.

(10) Patent No.: US 7,005,526 B2
(45) Date of Patent: Feb. 28, 2006

(54) THIOETHER DERIVATIVES

(75) Inventors: Birgit Bossenmaier, Seefeld (DE); Walter-Gunar Friebe, Mannheim (DE); Thomas Friess, Planegg (DE); Lothar Kling, Mannheim (DE); Ulrike Reiff, Penzberg (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/132,082

(22) Filed: May 18, 2005

(65) Prior Publication Data

US 2005/0267179 A1    Dec. 1, 2005

(30) Foreign Application Priority Data

May 25, 2004 (EP) ................... 04012294
Dec. 9, 2004 (EP) ................... 04029138

(51) Int. Cl.
*C07D 263/32* (2006.01)
*C07D 249/04* (2006.01)
*A61K 31/422* (2006.01)
*A61K 31/4192* (2006.01)

(52) U.S. Cl. .............. 548/235; 514/374; 514/383; 548/255

(58) Field of Classification Search .......... 548/255, 548/235; 514/383, 374
See application file for complete search history.

(56) References Cited

FOREIGN PATENT DOCUMENTS

| | | |
|---|---|---|
| EP | 1270571 | 1/2003 |
| WO | WO 98/03505 | 1/1998 |
| WO | WO 01/77107 | 10/2001 |
| WO | WO 03/031442 | 4/2003 |
| WO | WO 03/059907 | 7/2003 |
| WO | WO 2004/085434 | 10/2004 |

OTHER PUBLICATIONS

Wilks et al., Progress in Growth Factor Reseach, 2, pp. 97-111 (1990).
Chan et a., Cur. Opin. in Immunol., 8, pp. 394-401 (1995).
Yarden et al., Ann. Rev. Biochem., 57, pp. 443-478 (1988).
Wright et al., Br. J. Cancer, 65, pp. 118-121 (1992).
Baselga et al., Oncology, 63 (Suppl. 1), pp. 6-16 (2002).
Ranson et al., Oncology, 63 (Suppl. 1), pp. 17-24 (2002).
Bastin et al., Organic Proc. Res. Dev., 4, pp. 427-435 (2000).
Coolen et al., Recl. Trav. Chim. Pays-Bas., 114 pp. 381-386 (1995).

*Primary Examiner*—Kamal A. Saeed
*Assistant Examiner*—Michael P. Barker
(74) *Attorney, Agent, or Firm*—George W. Johnston; Patricia S. Rooha-Tramaloni; Brian C. Remy

(57) ABSTRACT

Objects of the present invention are the compounds of formula (I) formula (I),

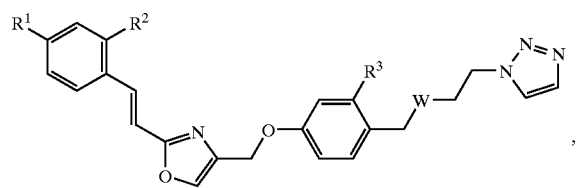

formula (I)

their pharmaceutically acceptable salts, enantiomeric forms, diastereoisomers and racemates, the preparation of the above compounds, pharmaceutical compositions containing them and their manufacture, as well as the use of the above compounds in the control or prevention of illnesses such as cancer.

16 Claims, No Drawings

THIOETHER DERIVATIVES

PRIORITY TO RELATED APPLICATIONS

This application claims the benefit of European Application No. 04012294.7, filed May 25, 2004, and European Application No. 04029138.7, filed Dec. 9, 2004, which are both incorporated herein by reference in their entirety.

FIELD OF THE INVENTION

The present invention relates to novel thioether derivatives, to a process for their manufacture, pharmaceutical compositions containing them and their manufacture as well as the use of such compounds as pharmaceutically active agents.

BACKGROUND OF THE INVENTION

Protein tyrosine kinases (PTKs) catalyse the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394–401). Such PTKs can be divided into receptor tyrosine kinases (e.g. EGFR/HER-1, c-erB2/HER-2, c-met, PDGFr, FGFr) and non-receptor tyrosine kinases (e.g. src, lck). It is known that many oncogenes encode proteins which are aberrant tyrosine kinases capable of causing cell transformation (Yarden, Y., and Ullrich, A., Annu. Rev. Biochem. 57 (1988) 443–478; Larsen et al., Ann. Reports in Med. Chem., 1989, Chpt. 13). Also over-expression of a normal proto-oncogenic tyrosine kinase may result in proliferative disorders.

It is known that receptor tyrosine kinases of the HER-family like HER-2 and EGFR (HER1) are frequently aberrantly expressed in common human cancers such as breast cancer, gastrointestinal cancer (colon, rectal or stomach cancer), leukemia and ovarian, bronchial and pancreatic cancer. High levels of these receptors correlate with poor prognosis and response to treatment (Wright, C., et al., Br. J. Cancer 65 (1992) 118–121).

Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6–16; Ranson, M., and Sliwkowski, M. X., Oncology 63 (suppl. 1) (2002) 17–24).

Some substituted oxazoles are known in the art. WO 98/03505, EP 1 270 571, WO 01/77107, WO 03/031442 and WO 03/059907 disclose related heterocyclic compounds as tyrosine kinase inhibitors.

However, there remains a need for new compounds with improved therapeutic properties, such as enhanced activity, decreased toxicity, better solubility and improved pharmacokinetic profile, to name only a few.

SUMMARY OF THE INVENTION

The present invention relates to compounds of general formula I and pharmaceutically acceptable salts or esters thereof wherein formula I is:

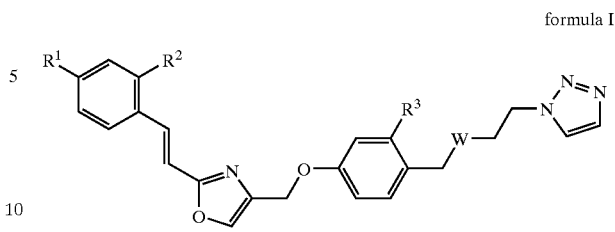

formula I wherein:
(a) $R^1$ is selected from the group consisting of:
  (1) halogenated alkoxy;
  (2) halogenated alkylsulfanyl;
  (3) halogenated alkyl; and
  (4) halogen;
(b) $R^2$ is selected from the group consisting of:
  (1) hydrogen; and
  (2) halogen;
(c) $R^3$ is selected from the group consisting of:
  (1) hydrogen; and
  (2) alkyl; and
(d) W is selected from the group consisting of:
  (1) —S—;
  (2) —S(O)—; and
  (3) —S(O)$_2$—.

The compounds of formula I are useful for preventing or treating proliferative diseases and conditions such as tumor growth and cancer including, but not limited to, breast cancer, leukemia, ovarian cancer, bronchial or lung cancer, pancreatic cancer, and gastrointestinal cancer such as colon cancer, rectal cancer, and stomach cancer.

The compounds of the present invention show activity as inhibitors of the HER-signalling pathway and therefore possess anti-proliferative activity. The present invention provides compounds of formula I and their pharmaceutically acceptable salts or esters, enantiomeric forms, diastereoisomers and racemates, the preparation of the above-mentioned compounds, compositions containing them and their manufacture as well as the use of the above-mentioned compounds in the control or prevention of illnesses, especially of illnesses and disorders as mentioned above like common human cancers (e.g. breast cancer, gastrointestinal cancer (colon, rectal or stomach cancer), leukemia and ovarian, bronchial and pancreatic cancer) or in the manufacture of corresponding pharmaceutical compositions.

DETAILED DESCRIPTION OF THE INVENTION

As used herein, the term "alkyl" means a saturated, straight-chain or branched-chain hydrocarbon containing from 1 to 4, preferably 1 or 2, carbon atoms. Examples are methyl, ethyl, n-propyl, isopropyl, n-butyl, sec-butyl or tert-butyl.

As used herein, the term "halogenated alkyl" means an alkyl group as defined above which is substituted with one or several halogen atoms, preferably fluorine or chlorine, more preferably fluorine. Examples are trifluoromethyl, 2,2,2-trifluoroethyl, perfluoroethyl and the like; preferably trifluoromethyl.

As used herein, the term "fluorinated alkyl" means an alkyl group as defined above which is substituted with one or several fluorine atoms. Examples are trifluoromethyl, 2,2,2-trifluoroethyl, perfluoroethyl and the like; preferably trifluoromethyl.

As used herein, the term "halogenated alkoxy" means a halogenated alkyl group as defined above which is attached via an oxygen atom. Examples are difluoromethoxy, trifluoromethoxy, 2,2,2-trifluoroethoxy, perfluoroethoxy and the like; preferably trifluoromethoxy.

As used herein, the term "halogenated alkylsulfanyl" means a halogenated alkyl group as defined above which is attached via a sulfur atom. Examples are difluoromethylsulfanyl, trifluoromethylsulfanyl, 2,2,2-trifluoroethylsulfanyl, perfluoroethylsulfanyl and the like; preferably trifluoromethyl-sulfanyl.

As used herein, when referring to the receptor tyrosine kinases of the HER-family like HER-2 and EGFR (HER-1), the acronym "HER" refers to human epidermal receptor and the acronym "EGFR" refers to epidermal growth factor receptor.

As used herein, "THF" refers to tetrahydrofuran.

As used herein, "EGTA" refers to Ethylene glycol-bis(2-aminoethylether)-N,N,N',N'-tetraacetic acid.

As used herein, "PMSF" refers to Phenylmethylsulfonyl fluoride.

As used herein, "DMSO" refers to N,N-dimethylsulfoxide.

As used herein, the term "DMF" refers to N,N-dimethyl formamide.

As used herein, "Hepes" refers to 4-(2-Hydroxyethyl)-1-piperazineethanesulfonic acid.

As used herein, in relation to nuclear magnetic resonance (NMR) the term "$D_6$-DMSO" refers to deuterated N,N-dimethylsulfoxide.

As used herein, in relation to mass spectrometry (MS) the term "ESI+" refers to positive electrospray ionization mode and the term "API+" refers to positive atmospheric pressure ionization mode.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The compounds according to the present invention may exist in the form of their pharmaceutically acceptable salts or esters. The term "pharmaceutically acceptable salt" refers to conventional acid-addition salts that retain the biological effectiveness and properties of the compounds of formula I and are formed from suitable non-toxic organic or inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g. Bastin, R. J., et al., Organic Proc. Res. Dev. 4 (2000) 427–435.

Preferred are the pharmaceutically acceptable salts, which are formed with p-toluenesulfonic acid, naphthalenesulfonic acid, naphthalenedisulfonic acid, methanesulfonic acid and hydrochloric acid.

Preferred substituents in $R^1$ of formula I are trifluoromethoxy, difluoromethoxy, trifluoromethylsulfanyl, chlorine and trifluoromethyl.

In a preferred embodiment, the term "halogen" as used in $R^1$ denotes fluorine or chlorine, preferably chlorine and the term "halogen" as used in $R^2$ denotes fluorine or chlorine, preferably fluorine.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

In another preferred embodiment, $R^2$ of formula I is preferably hydrogen or fluorine.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein $R^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein $R^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein $R^1$ is halogenated alkoxy or halogenated alkylsulfanyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein:
(a) $R^1$ is selected from the group consisting of:
   (1) halogenated alkoxy; and
   (2) halogenated alkylsulfanyl; and
(b) $R^2$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein:
(a) $R^1$ is selected from the group consisting of:
   (1) halogenated alkoxy; and
   (2) halogenated alkylsulfanyl; and
(b) $R^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein:
(a) $R^1$ is selected from the group consisting of:
   (1) halogenated alkoxy; and
   (2) halogenated alkylsulfanyl;
(b) $R^2$ is hydrogen; and
(c) $R^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Such compounds are for example:
1-[2-(4-{2-[2-(4-Trifluoromethoxy-phenyl)-vinyl]-oxazol-4-ylmethoxy}-benzylsulfanyl)-ethyl]-1H-[1,2,3]triazole;
1-[2-(4-{2-[2-(4-Trifluoromethoxy-phenyl)-vinyl]-oxazol-4-ylmethoxy}-phenylmethanesulfonyl)-ethyl]-1H-[1,2,3]triazole;
1-[2-(4-{2-[2-(4-Trifluoromethylsulfanyl-phenyl)-vinyl]-oxazol-4-ylmethoxy}-phenylmethanesulfinyl)-ethyl]-1H-[1,2,3]triazole; and
1-[2-(4-{2-[2-(4-Difluoromethoxy-phenyl)-vinyl]-oxazol-4-ylmethoxy}-phenylmethanesulfinyl)-ethyl]-1H-[1,2,3]triazole.

A preferred embodiment of the present invention is the compound:
1-[2-(4-{2-[2-(4-Trifluoromethoxy-phenyl)-vinyl]-oxazol-4-ylmethoxy}phenylmethanesulfinyl)-ethyl]-1H-[1,2,3]triazole.

Another preferred embodiment are the compounds of formula I, wherein:
(a) $R^1$ is selected from the group consisting of:
   (1) halogenated alkoxy; and
   (2) halogenated alkylsulfanyl; and
(b) $R^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein:
(a) $R^1$ is selected from the group consisting of:
   (1) halogenated alkoxy; and
   (2) halogenated alkylsulfanyl;
(b) $R^2$ is hydrogen; and
(c) $R^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein $R^1$ is halogenated alkoxy.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—;

Another preferred embodiment are the compounds of formula I, wherein $R^1$ is halogenated alkoxy and $R^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein $R^1$ is halogenated alkoxy and $R^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein $R^1$ is halogenated alkoxy; $R^2$ is hydrogen; and $R^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein $R^1$ is halogenated alkoxy; $R^2$ is hydrogen; and $R^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Such compounds are for example:
1-[2-(2-Methyl-4-{2-[(E)-2-(4-trifluoromethoxy-phenyl)-vinyl]-oxazol-4-ylmethoxy}-phenylmethanesulfanyl)-ethyl]-1H-[1,2,3]triazole;
1-[2-(2-Methyl-4-{2-[(E)-2-(4-trifluoromethoxy-phenyl)-vinyl]-oxazol-4-ylmethoxy}-phenylmethanesulfinyl)-ethyl]-1H-[1,2,3]triazole; and
1-[2-(2-Methyl-4-{2-[(E)-2-(4-trifluoromethoxy-phenyl)-vinyl]-oxazol-4-ylmethoxy}-phenylmethanesulfonyl)-ethyl]-1H-[1,2,3]triazole.

Another preferred embodiment are the compounds of formula I, wherein $R^1$ is halogenated alkylsulfanyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Still another preferred embodiment are the compounds of formula I, wherein $R^1$ is halogenated alkylsulfanyl and $R^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Still another preferred embodiment are the compounds of formula I, wherein R$^1$ is halogenated alkylsulfanyl and R$^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Still a preferred embodiment of the invention are the compounds of formula I, wherein:
  (a) R$^1$ is selected from the group consisting of:
    (1) halogenated alkyl; and
    (2) halogen; and
  (b) R$^2$ is selected from the group consisting of:
    (1) hydrogen; and
    (2) fluorine.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Still a preferred embodiment of the invention are the compounds of formula I, wherein:
  (a) R$^1$ is selected from the group consisting of:
    (1) halogenated alkyl; and
    (2) halogen;
  (b) R$^2$ is selected from the group consisting of:
    (1) hydrogen; and
    (2) fluorine; and
  (c) R$^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Still a preferred embodiment of the invention are the compounds of formula I, wherein:
  (a) R$^1$ is selected from the group consisting of:
    (1) halogenated alkyl; and
    (2) halogen;
  (b) R$^2$ is selected from the group consisting of:
    (1) hydrogen; and
    (2) fluorine; and
  (c) R$^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein R$^1$ is halogenated alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein R$^1$ is halogenated alkyl and R$^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein R$^1$ is halogenated alkyl; R$^2$ is hydrogen; and R$^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Such a compound is for example:
1-[2-(4-{2-[2-(4-Trifluoromethyl-phenyl)-vinyl]-oxazol-4-ylmethoxy}-benzylsulfanyl)-ethyl]-1H-[1,2,3]triazole.

Another preferred embodiment are the compounds of formula I, wherein R$^1$ is halogenated alkyl; R$^2$ is fluorine; and R$^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Such a compound is for example:
1-[2-(4-{2-[2-(2-Fluoro-4-trifluoromethyl-phenyl)-vinyl]-oxazol-4-ylmethoxy}-benzylsulfanyl)-ethyl]-1H-[1,2,3]triazole.

A preferred embodiment of the present invention is the compound:
1-[2-(4-{2-[2-(2-Fluoro-4-trifluoromethyl-phenyl)-vinyl]-oxazol-4-ylmethoxy}-phenylmethanesulfinyl)-ethyl]-1H-[1,2,3]triazole.

Another preferred embodiment of the present invention is the compound: 1-[2-(4-{2-[2-(2-Fluoro-4-trifluoromethyl-phenyl)-vinyl]-oxazol-4-ylmethoxy}-phenylmethanesulfonyl)-ethyl]-1H-[1,2,3]triazole.

Another preferred embodiment are the compounds of formula I, wherein R$^1$ is halogenated alkyl and R$^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein R$^1$ is halogenated alkyl; R$^2$ is hydrogen; and R$^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein R$^1$ is halogenated alkyl; R$^2$ is fluorine; and R$^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Such compounds are for example:
1-[2-(4-{2-[(E)-2-(2-Fluoro-4-trifluoromethyl-phenyl)-vinyl]-oxazol-4-ylmethoxy}-2-methyl-phenylmethanesulfanyl)-ethyl]-1H-[1,2,3]triazole;
1-[2-(4-{2-[(E)-2-(2-Fluoro-4-trifluoromethyl-phenyl)-vinyl]-oxazol-4-ylmethoxy}-2-methyl-phenylmethanesulfinyl)-ethyl]-1H-[1,2,3]triazole; and
1-[2-(4-{2-[(E)-2-(2-Fluoro-4-trifluoromethyl-phenyl)-vinyl]-oxazol-4-ylmethoxy}-2-methyl-phenylmethanesulfonyl)-ethyl]-1H-[1,2,3]triazole.

Another preferred embodiment are the compounds of formula I, wherein R$^1$ is halogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein $R^1$ is halogen and $R^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein $R^1$ is halogen; $R^2$ is hydrogen; and $R^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Such a compound is for example:
1-[2-(4-{2-[2-(4-Chloro-phenyl)-vinyl]-oxazol-4-ylmethoxy}-benzylsulfanyl)-ethyl]-1H-[1,2,3]triazole.

Another preferred embodiment are the compounds of formula I, wherein $R^1$ is halogen; $R^2$ is fluorine; and $R^3$ is hydrogen.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Such compounds are for example:
1-[2-(4-{2-[2-(4-Chloro-2-fluoro-phenyl)-vinyl]-oxazol-4-ylmethoxy}-benzylsulfanyl)-ethyl]-1H-[1,2,3]triazole;
1-[2-(4-{2-[2-(4-Chloro-2-fluoro-phenyl)-vinyl]-oxazol-4-ylmethoxy}-phenylmethanesulfinyl)-ethyl]-1H-[1,2,3]triazole and
1-[2-(4-{2-[2-(4-Chloro-2-fluoro-phenyl)-vinyl]-oxazol-4-ylmethoxy}-phenylmethanesulfonyl)-ethyl]-1H-[1,2,3]triazole.

Another preferred embodiment are the compounds of formula I, wherein $R^1$ is halogen and $R^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein $R^1$ is halogen; $R^2$ is hydrogen; and $R^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Another preferred embodiment are the compounds of formula I, wherein $R^1$ is halogen; $R^2$ is fluorine; and $R^3$ is alkyl.

In a more specific embodiment of the preceding preferred embodiment, W is —S—. In another specific embodiment of the preceding preferred embodiment, W is —S(O)—. In a further specific embodiment of the preceding preferred embodiment, W is —S(O)$_2$—.

Such compounds are for example:
1-[2-(4-{2-[(E)-2-(4-Chloro-2-fluoro-phenyl)-vinyl]-oxazol-4-ylmethoxy}-2-methyl-phenylmethanesulfanyl)-ethyl]-1H-[1,2,3]triazole;
1-[2-(4-{2-[(E)-2-(4-Chloro-2-fluoro-phenyl)-vinyl]-oxazol-4-ylmethoxy}-2-methyl-phenylmethanesulfinyl)-ethyl]-1H-[1,2,3]triazole; and
1-[2-(4-{2-[(E)-2-(4-Chloro-2-fluoro-phenyl)-vinyl]-oxazol-4-ylmethoxy}-2-methyl-phenylmethanesulfonyl)-ethyl]-1H-[1,2,3]triazole.

Yet another embodiment of the present invention are the compounds of formula I, wherein W is —S—.

Yet another embodiment of the present invention are the compounds of formula I, wherein $R^3$ is hydrogen and W is —S—.

Yet another embodiment of the present invention are the compounds of formula I, wherein $R^3$ is alkyl and W is —S—.

Yet another embodiment of the present invention are the compounds of formula I, wherein:
(a) $R^1$ is selected from the group consisting of:
  (1) halogenated alkoxy; and
  (2) halogenated alkylsulfanyl; and
(b) W is —S—.

Yet another embodiment of the present invention are the compounds of formula I, wherein:
(a) $R^1$ is selected from the group consisting of:
  (1) halogenated alkoxy; and
  (2) halogenated alkylsulfanyl;
(b) $R^3$ is hydrogen; and
(c) W is —S—.

Yet another embodiment of the present invention are the compounds of formula I, wherein:
(a) $R^1$ is selected from the group consisting of:
  (1) halogenated alkoxy; and
  (2) halogenated alkylsulfanyl;
(b) $R^3$ is alkyl; and
(c) W is —S—.

Yet another embodiment of the invention are the compounds of formula I, wherein:
(a) $R^1$ is selected from the group consisting of:
  (1) halogenated alkyl; and
  (2) halogen;
(b) $R^2$ is selected from the group consisting of:
  (1) hydrogen; and
  (2) fluorine; and
(c) W is —S—.

Yet another embodiment of the invention are the compounds of formula I, wherein:
(a) $R^1$ is selected from the group consisting of:
  (1) halogenated alkyl; and
  (2) halogen;
(b) $R^2$ is selected from the group consisting of:
  (1) hydrogen; and
  (2) fluorine;
(c) $R^3$ is hydrogen; and
(d) W is —S—.

Yet another embodiment of the invention are the compounds of formula I, wherein:
(a) $R^1$ is halogenated alkyl; preferably fluorinated alkyl;
(b) $R^2$ is selected from the group consisting of:
  (1) hydrogen; and
  (2) fluorine;
(c) $R^3$ is hydrogen; and
(d) W is —S—.

Yet another embodiment of the invention are the compounds of formula I, wherein:
(a) $R^1$ is halogenated alkyl;
(b) $R^2$ is selected from the group consisting of:
  (1) hydrogen; and
  (2) fluorine;

(c) $R^3$ is alkyl; and
(d) W is —S—.

Yet another embodiment of the present invention are the compounds of formula I, wherein W is —S(O)—.

Yet another embodiment of the present invention are the compounds of formula I, wherein $R^3$ is hydrogen and W is —S(O)—.

Yet another embodiment of the present invention are the compounds of formula I, wherein $R^3$ is alkyl and W is —S(O)—.

Yet another embodiment of the present invention are the compounds of formula I, wherein:
(a) $R^1$ is selected from the group consisting of:
  (1) halogenated alkoxy; and
  (2) halogenated alkylsulfanyl; and
(b) W is —S(O)—.

Yet another embodiment of the present invention are the compounds of formula I, wherein:
(a) $R^1$ is selected from the group consisting of:
  (1) halogenated alkoxy; and
  (2) halogenated alkylsulfanyl;
(b) $R^3$ is hydrogen; and
(c) W is —S(O)—.

Yet another embodiment of the present invention are the compounds of formula I, wherein:
(a) $R^1$ is selected from the group consisting of:
  (1) halogenated alkoxy; and
  (2) halogenated alkylsulfanyl;
(b) $R^3$ is alkyl; and
(c) W is —S(O)—.

Yet another embodiment of the invention are the compounds of formula I, wherein:
(a) $R^1$ is selected from the group consisting of:
  (1) halogenated alkyl; and
  (2) halogen;
(b) $R^2$ is selected from the group consisting of:
  (1) hydrogen; and
  (2) fluorine; and
(c) W is —S(O)—.

Yet another embodiment of the invention are the compounds of formula I, wherein:
(a) $R^1$ is selected from the group consisting of:
  (1) halogenated alkyl; and
  (2) halogen;
(b) $R^2$ is selected from the group consisting of:
  (1) hydrogen; and
  (2) fluorine;
(c) $R^3$ is hydrogen; and
(d) W is —S(O)—.

Yet another embodiment of the invention are the compounds of formula I, wherein:
(a) $R^1$ is halogenated alkyl; preferably fluorinated alkyl;
(b) $R^2$ is selected from the group consisting of:
  (1) hydrogen; and
  (2) fluorine;
(c) $R^3$ is hydrogen; and
(d) W is —S(O)—.

Yet another embodiment of the invention are the compounds of formula I, wherein:
(a) $R^1$ is halogenated alkyl;
(b) $R^2$ is selected from the group consisting of:
  (1) hydrogen; and
  (2) fluorine;
(c) $R^3$ is alkyl; and
(d) W is —S(O)—.

Yet another embodiment of the present invention are the compounds of formula I, wherein W is —S(O)$_2$—.

Yet another embodiment of the present invention are the compounds of formula I, wherein $R^3$ is hydrogen and W is —S(O)$_2$—.

Yet another embodiment of the present invention are the compounds of formula I, wherein $R^3$ is alkyl and W is —S(O)$_2$—.

Yet another embodiment of the present invention are the compounds of formula I, wherein:
(a) $R^1$ is selected from the group consisting of:
  (1) halogenated alkoxy; and
  (2) halogenated alkylsulfanyl; and
(b) W is —S(O)$_2$—.

Yet another embodiment of the present invention are the compounds of formula I, wherein:
(a) $R^1$ is selected from the group consisting of:
  (1) halogenated alkoxy; and
  (2) halogenated alkylsulfanyl;
(b) $R^3$ is hydrogen; and
(c) W is —S(O)$_2$—.

Yet another embodiment of the present invention are the compounds of formula I, wherein:
(a) $R^1$ is selected from the group consisting of:
  (1) halogenated alkoxy; and
  (2) halogenated alkylsulfanyl;
(b) $R^3$ is alkyl; and
(c) W is —S(O)$_2$—.

Yet another embodiment of the invention are the compounds of formula I, wherein:
(a) $R^1$ is selected from the group consisting of:
  (1) halogenated alkyl; and
  (2) halogen;
(b) $R^2$ is selected from the group consisting of:
  (1) hydrogen; and
  (2) fluorine; and
(c) W is —S(O)$_2$—.

Yet another embodiment of the invention are the compounds of formula I, wherein:
(a) $R^1$ is selected from the group consisting of:
  (1) halogenated alkyl; and
  (2) halogen;
(b) $R^2$ is selected from the group consisting of:
  (1) hydrogen; and
  (2) fluorine;
(c) $R^3$ is hydrogen; and
(d) W is —S(O)$_2$—.

Yet another embodiment of the invention are the compounds of formula I, wherein:
(a) $R^1$ is halogenated alkyl; preferably fluorinated alkyl;
(b) $R^2$ is selected from the group consisting of:
  (1) hydrogen; and
  (2) fluorine;
(c) $R^3$ is hydrogen; and
(d) W is —S(O)$_2$—.

Yet another embodiment of the invention are the compounds of formula I, wherein:
(a) $R^1$ is halogenated alkyl;
(b) $R^2$ is selected from the group consisting of:
  (1) hydrogen; and
  (2) fluorine;
(c) $R^3$ is alkyl; and
(d) W is —S(O)$_2$—.

Still another embodiment of the invention is a process for the manufacture of the compounds of formula I, wherein:

(a) the compound of formula V

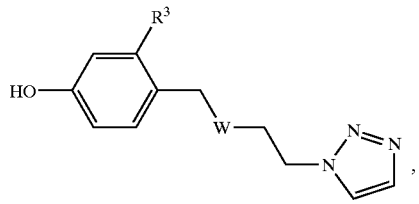

wherein $R^3$ and W has the significance as given in formula I above, is reacted with a compound of formula IV formula IV wherein $R^1$ and $R^2$ have the significance given, to give the respective compound of formula I;

(b) said compound of formula I is isolated from the reaction mixture, and (c) if desired, converted into a pharmaceutically acceptable salt.

The derivatives of the general formula I, wherein W is —S—; —S(O)— or —S(O)$_2$—, or a pharmaceutically acceptable salt thereof, may be prepared by any process known to be applicable for the preparation of chemically-related compounds by the one skilled in the art. Such processes, when used to prepare the thioether derivatives of formula I, or a pharmaceutically-acceptable salt thereof, are provided as a further feature of the invention and are illustrated by the following representative examples of scheme 1, in which, unless otherwise stated $R^1$, $R^2$ and W have the significance given herein before. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

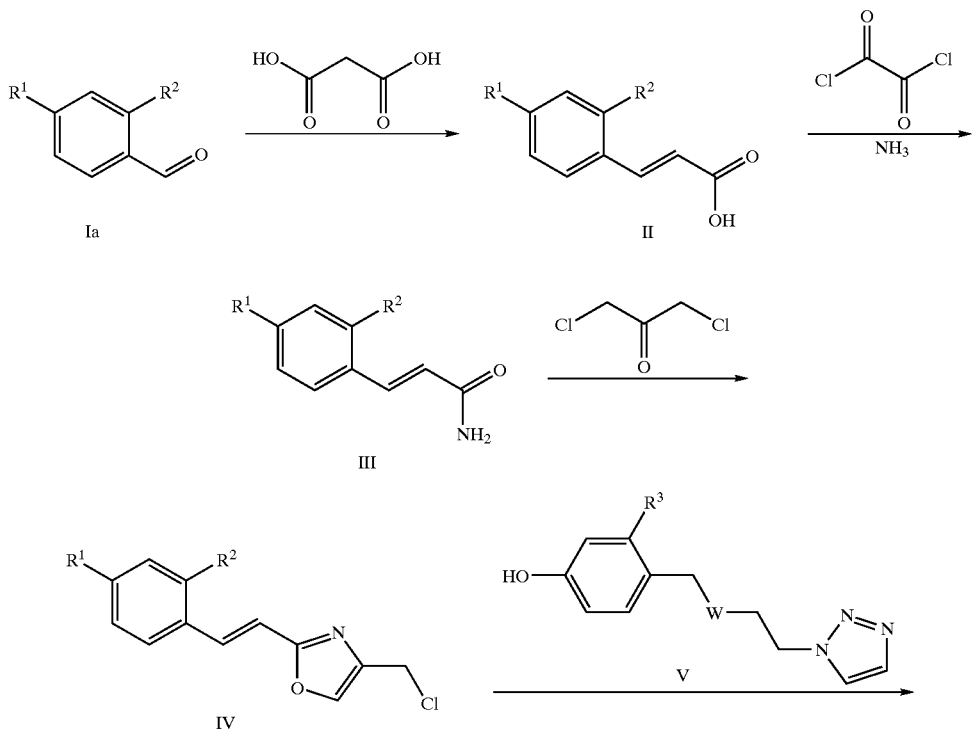

-continued

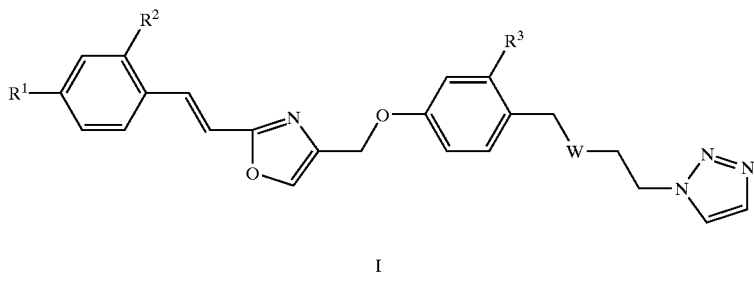

I

A preferred method for the synthesis of the compounds of formula I is described in scheme 1, and starts from the corresponding benzaldehydes formula Ia wherein the $R^1$ and $R^2$ have significance as given above in formula I. The first step of the reaction sequence is a Knoevenagel condensation with malonic acid and concomitant decarboxylation, yielding acrylic acids of formula II. The reaction is typically carried out in solvents like pyridine, N-methylpyrrolidinone (NMP), acetonitrile, N,N-dimethylformamide (DMF) and mixtures thereof at temperatures up to 140° C. Typically used bases are piperidine, triethylamine and diisopropylamine.

The obtained acrylic acids of formula II are converted into their corresponding amides of formula III by standard methods for someone skilled in the art, e.g. by activating the carboxylic group in formula II with oxalyl chloride in solvents like tetrahydrofuran (THF), dichloromethane, N,N-dimethylformamide and mixtures thereof at temperatures varying from −30° C. to 40° C. The addition of ammonia yields said amides of formula III.

Chlorides of formula IV can be synthesized by a commonly known method or a modification thereof. Amides of formula III and 1,3-dichloroacetone are subjected to a condensation/dehydration sequence yielding the compounds of formula IV. Typical solvents for reactions of this kind are toluene, xylene, benzene, acetone and chloroform. If desired, the reaction can be carried out under solvent free conditions. The reaction temperatures may vary from 50° C. to 150° C.

The derivatives of formula I, wherein W is —S—; —S(O)— or —S(O)$_2$—, can be obtained by reactions well known to someone skilled in the art, e.g. by alkylation of compounds of formula V with compounds of formula IV according to scheme 1. Typically the alkylation is carried out in the presence of potassium iodide or sodium iodide in solvents like N,N-dimethylformamide (DMF), methanol, ethanol and isopropanol. Typical bases for this reaction are sodium methylate, sodium hydride or lithium diisopropyl amide. The reaction temperatures may vary from 50° C. to 150° C.

The phenolic intermediates of formula V may be prepared by
(a) reaction of a compound of formula VI with a compound of formula VII

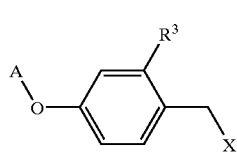
formula VI

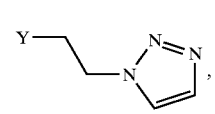
formula VII wherein $R^3$ has meaning given above in formula I, and
A denotes a suitable protecting group as defined below,
X denotes a thiol group and
Y denotes a suitable leaving group as defined below, to yield the corresponding thioether,
(b) an optional oxidation of the thioether to yield a sulfoxide or a sulfone, and
(c) subsequent removal of the protecting group A.

Reactions of compounds of formula VI with compounds of formula VII are well known in the art. Typically, such alkylation reaction may be carried out in solvents like DMF, methanol, ethanol and isopropanol. Typical bases for this reaction are alkaline carbonates, sodium methylate, sodium hydride or lithium diisopropyl amide. The reaction temperatures may vary from 20° C. to 150° C. Other preferred alkylation procedures make use of alkaline carbonates as bases in solvents like ketones, for example cesium carbonate in butanone at reflux temperature, or sodium hydride in DMF at room temperature. Suitable leaving groups Y are those typically used in alkylation reactions and well known to the skilled artisan. Examples of such leaving groups are, among others, the anions of halogens, especially iodide, bromide or chloride, p-toluenesulfonate (tosylate), methanesulfonate (mesylate), trifluoromethansulfonate (triflate) or the azido group.

The hydroxy protecting group A as mentioned herein is a conventional protecting group as known by the skilled artisan. Examples are tert-butoxycarbonyl (boc), propen-3-yl (allyl), triphenylmethyl (trityl) and silyl groups, e.g. tert-butyl-dimethyl-silyl, triisopropyl-silyl. Removal of a protecting group on a hetero atom depends on the nature of such group. Typical examples are the removal of a trityl group under acidic conditions, for example with aqueous formic acid in tetrahydrofuran (THF) under reflux or the removal of a tert-butoxycarbonyl group with trifluoroacetic acid in dichloromethane at room temperature or the removal of a substituted silyl group with tetrabutylammonium fluoride in aqueous THF at room temperature. An allyl group can smoothly be removed by treating the substrate with catalytic amounts of a palladium complex, e.g. Pd(PPh$_3$)$_4$ in dichloromethane in presence of an allyl-acceptor such as 1,3-dimethylbarbituric acid.

Compounds of formula V are new and also subject of this invention.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

The compounds of formula I and their pharmaceutically acceptable salts or esters possess valuable pharmacological properties. It has been found that said compounds inhibit the HER-signalling pathway and show anti-proliferative activity. Consequently the compounds of the present invention are useful in the therapy and/or prevention of illnesses with known over-expression of receptor tyrosine kinases of the HER-family like HER-2 and EGFR (HER1), especially in the therapy and/or prevention of illnesses mentioned above. The activity of the present compounds as HER-signalling pathway inhibitors is demonstrated by the following biological assay:

Inhibition of HER-2 Phosphorylation in Calu-3 Tumor Cell Line

2×10$^5$ Calu-3 (ATTC HTB-55) cells per well were plated in a 12-well plate. After 4 days cells were starved for 16 h in Dulbecco's Modified Eagle Medium (DMEM)/0.5% Fetal Calf Serum (FCS)/1% Glutamine. During this 16 h period cells were incubated with a solution of the test compound in dimethylsulfoxide (DMSO), so that the final concentration of the compound is 1 $\mu$M and the final volume of DMSO is 0.5%. Afterwards cells were lysed in lyses buffer containing 1% octyl phenol ethoxylate (Triton®X-100), 10% Glycerol, 1 mM Ethylene glycol-bis(2-aminoethylether)-N,N,N',N'-tetraacetic acid (EGTA), 1.5 mM MgCl$_2$, 150 mM NaCl, 50 mM 4-(2-hydroxyethyl)-1-piperazineethanesulfonic acid (HEPES) buffer pH 7.5, 1 mM Phenylmethylsulfonyl fluoride (PMSF), 10 $\mu$g/mL Aprotinin (a naturally occurring protein that is obtained and purified from cow's lungs) and 0.4 mm Orthovanadate (Na$_3$VO$_4$). Cell lysates were analyzed on a Sodium Dodecyl Sulfate Polyacrylamide Gel Electrophoresis (SDS PAGE) and after transfer to a nitrocellulose membrane detected with an antibody specifically recognizing the pY 1248 in HER-2 (phosphorylated tyrosine residue 1248 of human epidermal receptor 2). After incubation with an anti rabbit antibody coupled to POD (Peroxidase available from Biorad, Munich, Germany) signals were detected by chemiluminescence (ECL, Amersham). Inhibition of HER-2 phosphorylation is calculated as percentage of the control, which is treated with DMSO only. This percentage was calculated according to the following formula: Inhibition in %=100−(Phosphorylated-HER2-Signal of Test Sample*100/Phosphorylated-HER2-Signal DMSO-control).

With all compounds a significant inhibition of HER-2-phosphorylation was detected, which is exemplified by the compounds shown in Table 1. The reference compound as used herein is 1-[4-(4-{2-[2-(4-Trifluoromethyl-phenyl)-vinyl]-oxazol-4-ylmethoxy}-phenyl)-butyl]-1H-[1,2,3]triazole (Example 4, p. 88, WO 01/77107).

TABLE 1

|  | Control (DMSO) | Percent inhibition of HER-2-phosphorylation (compound concentration 1 $\mu$M) |
|---|---|---|
| reference compound | 0 | 52.3 |
| example 6, 10 | 0 | 55–65 |
| example 1, 9 | 0 | 65–80 |
| example 3, 7, 11 | 0 | >80 |

In Vivo Assay on Tumor Inhibition:

To generate primary tumors, Non-Small-Cell Lung Cancer (NSCLC) (e.g. Calu-3 (ATTC HTB-55) or A549 (ATTC CCL-185)) cells (4–5.0×10$^6$ in a volume of 100 $\mu$l) are injected subcutaneously into the left flank of female SCID beige (Severe Combined Immunodeficient/beige mice available from Charles River, Sulzfeld, Germany) or BALB/c nude (BALB/c Nude Spontaneous Mutant Mice (homozygotes) available from Taconic Europe, Ry, Denmark) mice. The cells are thawed and expanded in vitro before use in the experiment. Mice are assigned to the treatment groups 14–21 days after cell injection. For grouping (n=10–15 mice per group), the animals are randomized to get a similar mean primary tumor volume of ca. 100–150 mm$^3$ per group. The test compounds are administered orally once per day as a suspension in 7.5% gelatine 0.22% NaCl with an administration volume of 10 ml/kg based on actual body weights. Treatment is initiated one day after staging, and carried out until day 20–50, the final day of the study. The subcutaneous primary tumors are measured twice weekly, starting prior to randomisation, in two dimensions (length and width) using an electronic caliper. The volume of the primary tumor is calculated using the formula: V[mm$^3$]=(length[mm]×width [mm]×width [mm])/2. In addition, the body weight of all animals is recorded at least twice weekly. Finally, at the end of the study the tumors are explanted and weighed.

The compounds according to this invention and their pharmaceutically acceptable salts or esters can be used as medicaments, e.g. in the form of pharmaceutical compositions. The pharmaceutical compositions can be administered orally, e.g. in the form of tablets, coated tablets, dragees, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. For example, lactose, corn starch or derivatives thereof, talc, stearic acids or it's salts and the like can be used as carriers for tablets, coated tablets, dragees and hard gelatine capsules. Suitable carriers for soft gelatine capsules are, for example, vegetable oils, waxes, fats, semi-solid and liquid polyols and the like. However, depending on the nature of the active substance carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions comprise e.g. the following:

a) Tablet Formulation (Wet Granulation):

| Item | Ingredients | Mg/tablet | | | |
|---|---|---|---|---|---|
| 1. | Compound of formula I | 5 | 25 | 100 | 500 |
| 2. | Lactose Anhydrous DTG (direct tabletting grade) | 125 | 105 | 30 | 150 |
| 3. | Sta-Rx 1500 (pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Micro Suspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 μm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenise.

The above described preparation yields micro-suspensions of the compounds of formula I with particle sizes between 1 and 10 μm. The suspensions are suitable for oral applications and can be used in the in vivo assay described above.

Pharmaceutical compositions containing a compound of the present invention or a pharmaceutically acceptable salt thereof and a therapeutically inert carrier are also an object of the present invention, as is a process for their production, which comprises bringing one or more compounds of the present invention and/or pharmaceutically acceptable salts or esters and, if desired, one or more other therapeutically valuable substances into a galenical administration form together with one or more therapeutically inert carriers.

In accordance with the invention the compounds of the present invention as well as their pharmaceutically acceptable salts or esters are useful in the control or prevention of illnesses. Based on their HER-signalling pathway inhibition and their antiproliferative activity, said compounds are useful for the treatment of diseases such as cancer in humans or animals and for the production of corresponding pharmaceutical compositions. The dosage depends on various factors such as manner of administration, species, age and/or individual state of health.

Another embodiment of the invention is pharmaceutical composition, containing one or more compounds of formula I together with pharmaceutically acceptable excipients.

Still another embodiment of the invention is said pharmaceutical composition for the inhibition of tumor growth.

Still another embodiment of the invention is the use of a compound of formula I for the treatment of cancer.

Still another embodiment of the invention is the use of a compound of formula I for the manufacture of corresponding pharmaceutical compositions for the inhibition of tumor growth.

The following examples and references are provided to aid the understanding of the present invention, the true scope of which is set forth in the appended claims. It is understood that modifications can be made in the procedures set forth without departing from the spirit of the invention.

EXAMPLES

Example 1

1-[2-(4-{2-[2-(4-Trifluoromethoxy-phenyl)-vinyl]-oxazol-4-ylmethoxy}-benzylsulfanyl)-ethyl]-1H-[1,2,3]triazole A mixture of 5.00 g (3.80 ml, 26.3 mmol) 4-trifluoromethoxy-benzaldehyde, 3.10 g (30.0 mmol) malonic acid, 0.26 g (3.0 mmol) piperidine and 15.0 ml pyridine was kept at reflux temperature until carbon dioxide development ceased (3 h). After cooling to room temperature the reaction mixture was poured onto 50 g ice and 15 ml 6N HCl. The precipitate was isolated, washed with water and dried. Yield: 5.20 g (85%) 3-(4-Trifluoromethoxy-phenyl)-acrylic acid.

$^1$H-NMR (400 MHz, D$_6$-DMSO): δ=6.57 (d, 1H, 2-H), 7.40 (d, 2H, 3'-/5'-H), 7.62 (d, 1H, 3-H), 7.84 (d, 2H, 2'-/6'-H), 12.5 (br, 1H, COOH).

To a suspension of 4.90 g (21.1 mmol) 3-(4-trifluoromethoxy-phenyl)-acrylic acid in 30.0 ml tetrahydrofuran and 0.3 ml N,N-dimethylformamide a solution of 2.70 ml (32.0 mmol) oxalyl chloride in 5.0 ml tetrahydrofuran was added dropwise at 0° C. within 10 min. Stirring was continued at 0–5° C. for 30 min. and 2 h at room temperature thereafter. The resulting solution was cooled to 0–5° C. again and then added within 15 min. to 75 ml of a 25% aqueous ammonia solution. After stirring for 30 min. the precipitated amide was collected, washed with water and dried at 40° C. in vacuo. Yield: 4.48 g (92%) 3-(4-Trifluoromethoxy-phenyl)-acrylamide.

MS: M=232.2(API+) $^1$H-NMR (400 MHz, D$_6$-DMSO): δ=6.63 (d, 1H, 2-H), 7.16 (br, 1H, NH), 7.42 (d, 2H, 3'-/5'-H), 7.45 (d, 1H, 3-H), 7.58 (br, 1H, NH), 7.70 (d, 2H, 2'-/6'-H).

4.28 g (18.5 mmol) 3-(4-Trifluoromethoxy-phenyl)-acrylamide, 2.80 g (22.2 mmol) dichloroacetone and 30.0 ml toluene were kept at reflux temperature for 16 h with continuous removal of water by use of a Dean-Stark trap (a water separator typically used in chemical reactions). After removal of solvents in vacuo, the residue was purified by chromatography on silica gel (eluent: heptane/ethyl acetate 20:1). All fractions containing the product were concentrated to a volume of 10 ml and the crystallized material isolated by filtration, washed with cold heptane and dried. Yield: 1.75 g (31%) 4-Chloromethyl-2-[2-(4-trifluoromethoxy-phenyl)-vinyl]-ox azole.

MS: M=304.2 (API+) $^1$H-NMR (400 MHz, D$_6$-DMSO): δ=4.71 (s, 2H, CH$_2$Cl), 7.21 (d, 1H, =CH), 7.40 (d, 2H, Ar—H), 7.58 (d, 1H, =CH), 7.87 (d, 2H, Ar—H), 8.19 (s, 1H, oxazole).

A solution of 294 mg (1.25 mmol) 4-(2-[1,2,3]triazol-1-yl-ethanesulfanylmethyl)-phenol in 7 ml N,N-dimethylformamide was treated with 32 mg (1.25 mmol) sodium hydride and stirred at room temperature for 15 min, then 380 mg (1.25 mmol) 4-chloromethyl-2-[2-(4-trifluoromethoxy-phenyl)-vinyl]-oxazole were added and stirring continued over night. After addition of 20 ml water, the precipitate was isolated, washed thoroughly with water, hot methanol, and ether, and dried in vacuo at 40° C. Yield: 435 mg (69%) 1-[2-(4-{2-[2-(E)-(4-Trifluoromethoxy-phenyl)-vinyl]-oxazol-4-ylmethoxy}-benzylsulfanyl)-ethyl]-1H-[1,2,3]triazole.

$^1$H-NMR (400 MHz, D$_6$-DMSO): δ=2.87 (t, 2H, CH$_2$—CH2-N), 3.66 (s, 2H, CH$_2$—Ph), 4.55 (t, 2H, CH$_2$-triazole), 5.01 (s, 2H, OCH$_2$-oxazole), 7.00 (d, 2H, 3'-,5'-H), 7.21 (d, 1H, =CH), 7.25 (d, 2H, 2'-,6'-H), 7.40 (d, 2H, Ar—H), 7.57 (d, 1H, =CH), 7.73 (s, 1H, triazole), 7.87 (d, 2H, Ar—H), 8.12 (s, 1H, triazole), 8.22 (s, 1H, 5-H-oxazole).

Example 2

1-[2-(4-{2-[2-(E)-(4-Trifluoromethoxy-phenyl)-vinyl]-oxazol-4-ylmethoxy}-phenylmethanesulfonyl)-ethyl]-1H-[1,2,3]triazole To a solution of 101 mg (0.20 mmol) 1-[2-(4-{2-[2-(E)-(4-trifluoromethoxy-phenyl)vinyl]-oxazol-4-ylmethoxy}1-benzylsulfanyl)-ethyl]-1H-[1,2,3]triazole in 8 ml methanol were added dropwise during 20 min 369 mg (0.60 mmol) oxone dissolved in 4 ml water. After 24 hours stirring at room temperature the volatiles were distilled off, the residue dissolved in dichloromethane, washed with sodium bicarbonate solution, dried and evaporated. Elution from silica with ethyl acetate/methanol 25:1 furnished 63 mg (59%) title compound as white solid.

$^1$H-NMR (400 MHz, D$_6$-DMSO): δ=3.70 (t, 2H, CH$_2$—CH2-N), 4.43 (s, 2H, CH$_2$—Ph), 4.81 (t, 2H, CH$_2$-triazole), 5.04 (s, 2H, OCH$_2$-oxazole), 7.08 (d, 2H; 3'-,5'-H), 7.21 (d, 1H, =CH), 7.32 (d, 2H, 2'-,6'-H), 7.40 (d, 2H, Ar—OCF$_3$), 7.57 (d, 1H, =CH), 7.75 (s, 1H, triazole), 7.87 (d, 2H, Ar—OCF$_3$), 8.18 (s, 1H, triazole), 8.24 (s, 1H, 5-H-oxazole).

Example 3

1-[2-(4-{2-[2-(E)-(4-Trifluoromethoxy-phenyl)-vinyl]-oxazol-4-ylmethoxy}-phenylmethanesulfinyl)-ethyl]-1H-[1,2,3]triazole To a solution of 101 mg (0.20 mmol) 1-[2-(4-{2-[2-(E)-(4-trifluoromethoxy-phenyl)vinyl]-oxazol-4-ylmethoxy}-benzylsulfanyl)-ethyl]-1H-[1,2,3]triazole in 8 ml dichloromethane at −30° C. were added dropwise during 20 min 54 mg (0.24 mmol) 3-chloro-benzenecarboperoxoic acid dissolved in 2 ml ethyl acetate. After 1 hour stirring at −30° C. the mixture was allowed to warm up over night, diluted with dichloromethane, washed with sodium bicarbonate solution, then with water, dried and evaporated. Elution from silica with ethyl acetate/methanol 9:1 furnished 77 mg (74%) title compound as off-white solid.

$^1$H-NMR (400 MHz, D$_6$-DMSO): δ=3.12 (quintet, 1H, CH$_2$—CH2-N), 3.34 (quintet, 1H, CH$_2$—CH2-N), 3.96 (d, 1H, CH$_2$—Ph), 4.14 (d, 1H, CH$_2$—Ph), 4.79 (t, 2H, CH$_2$-triazole), 5.03 (s, 2H, OCH$_2$-oxazole), 7.05 (d, 2H, 3'-,5'-H), 7.21 (d, 1H, =CH), 7.25 (d, 2H, 2'-,6'-H), 7.40 (d, 2H, Ar—H), 7.57 (d, 1H, =CH), 7.75 (s, 1H, triazole), 7.87 (d, 2H, Ar—H), 8.17 (s, 1H, triazole), 8.23 (s, 1H, 5-H-oxazole).

Example 4

1-[2-(4-{2-[2-(4-Trifluoromethylsulfanyl-phenyl)-vinyl]-oxazol-4-ylmethoxy}-phenylmethanesulfinyl)-ethyl]-1H-[1,2,3]triazole A mixture of 5.42 g (26.3 mmol) 4-trifluoromethylsulfanyl-benzaldehyde, 3.12 g (30.0 mmol) malonic acid, 0.26 g (3.0 mmol) piperidine and 12.0 ml pyridine was kept at reflux temperature until carbon dioxide development ceased (5 h). After cooling to room temperature, the reaction mixture was poured onto 50 g ice and 15 ml 6N HCl. The precipitate was isolated, washed with water and dried. Yield: 5.90 g (90%) 3-(4-Trifluoromethylsulfanyl-phenyl)-acrylic acid.

$^1$H-NMR (400 MHz, D$_6$-DMSO): δ=6.65 (d, 1H, 2-H), 7.63 (d, 1H, 3-H), 7.74 (d, 2H, 3'-/5'-H), 7.84 (d, 2H, 2'-/6'-H), 12.7 (br, 1H, COOH).

To a suspension of 5.24 g (21.1 mmol) 3-(4-trifluoromethylsulfanyl-phenyl)-acrylic acid in 30.0 ml tetrahydrofuran and 0.3 ml N,N-dimethylformamide a solution of 2.70 ml (32.0 mmol) oxalyl chloride in 5.0 ml tetrahydrofuran was added dropwise at 0° C. within 20 min. Stirring was continued at 0–5° C. for 30 min. and 3 h at room temperature thereafter. The resulting solution was cooled to 0–5° C. again and then added within 15 min. to 100 ml of a 25% aqueous ammonia solution. After evaporation of the organic solvent, 200 ml water were added and the solution cooled. The precipitated amide was collected, washed with water and dried at 40° C. in vacuo. Yield 4.62 g (89%) 3-(4-Trifluoromethylsulfanyl-phenyl)-acrylamide.

MS: M=248.2 (API+) $^1$H-NMR (400 MHz, D$_6$-DMSO): δ=6.72 (d, 1H, 2-H), 7.21 (br, 1H, NH), 7.46 (d, 1H, 3-H), 7.62 (br, 1H, NH), 7.73 (dd, 4H, Ar—H).

4.45 g (18.0 mmol) 3-(4-Trifluoromethylsulfanyl-phenyl)-acrylamide, 2.80 g (22.2 mmol) 1,3-dichloroacetone and 50.0 ml toluene were kept at reflux temperature for 40 h with continuous removal of water by use of a water separator (Dean-Stark trap). After removal of solvents in vacuo, the residue was purified by chromatography on silica gel (eluent: heptane/ethyl acetate 1:1). All fractions containing the product were concentrated to a volume of 10 ml and the crystallized material isolated by filtration, washed with cold heptane and dried. Yield 2.02 g (35%) 4-Chloromethyl-2-[2-(4-trifluoromethylsulfanyl-phenyl)vinyl]-oxazole.

MS: M=320.1 (API+) $^1$H-NMR (400 MHz, D$_6$-DMSO): δ=4.71 (s, 2H, CH$_2$Cl), 7.30 (d, 1H, =CH), 7.59 (d, 1H, =CH), 7.74 (d, 2H, Ar—H), 7.89 (d, 2H, Ar—H), 8.21 (s, 1H, oxazole).

A mixture of 19.6 g (107.3 mmol) 1-allyloxy-4-chloromethyl-benzene (Coolen, H. K. A. C., et al., Recl. Trav. Chim. Pays-Bas 114(1995) 381–386) and 8.99 g (118 mmol) thiourea in 25 ml ethanol was refluxed for 7 hours, then allowed to cool over night, evaporated and the residue washed with ethanol.

$^1$H-NMR (400 MHz, D$_6$-DMSO): δ=4.46 (s, 2H, CH$_2$S), 4.56 (d, 2H, OCH$_2$-vinyl), 5.26 (d, 1H, =CH$_2$), 5.38 (d, 1H, =CH$_2$), 6.03 (m, 1H, CH=CH$_2$), 6.95 (d, 2H, 3-H/5-H), 7.35 (d, 2H, 2-H/6-H), 9.24 (br, 4H, NH$_2$).

The obtained isothiuronium chloride was heated to reflux with 25 ml ethanol and 7.5 ml 25% ammonia for 2 hours, then evaporated and partitioned between 5 ml 6N HCl and ethyl acetate. The organic phase was dried and evaporated to leave 13.65 g (71%) (4-allyloxy-phenyl)-methanethiol as nearly colorless oil.

$^1$H-NMR (400 MHz, D$_6$-DMSO): δ=2.75 (s, 1H, SH), 3.68 (s, 2H, CH$_2$SH), 4.54 (d, 2H, OCH$_2$-vinyl), 5.24 (d, 1H, =CH$_2$), 5.38 (d, 1H, =CH$_2$), 6.03 (m, 1H, CH=CH$_2$), 6.88 (d, 2H, 3-H/5-H), 7.15 (d, 2H, 2-H/6-H).

To a solution of 12.90 g (66.3 mmol) toluene-4-sulfonylchloride, 8.12 g (80.2 mmol) triethylamine and 2.03 g (16.6 mmol) 4-(N,N-dimethylamino)-pyridine in 150 ml dichloromethane was dropped at −10° C. a solution of 7.5 g (66.3 mmol) 2-[1,2,3]triazol-1-yl-ethanol in 150 ml dichloromethane and stirring continued at −4° C. over night. After addition of 170 g ice, 280 ml water and 170 ml dichloromethane, 3.9 ml concentrated HCl were added. Vigorous stirring was followed by quick separation of the organic layer that was washed with sodium bicarbonate solution, then with sodium chloride solution, dried and evaporated. Yield: 15.3 g (86%) toluene-4-sulfonic acid 2-[1,2,3]triazol-1-yl-ethyl ester.

To a mixture of 13.0 g (50.5 mmol) (4-allyloxy-phenyl)-methanethiol and 13.5 g (50.5 mmol) toluene-4-sulfonic acid 2-[1,2,3]triazol-1-yl-ethyl ester in 125 ml N,N-dimethylformamide was added under argon at −30° C. 2.42 g (101 mmol) sodium hydride. The mixture was allowed to warm up to room temperature and was stirred under argon for 12 hours. After quenching with 100 ml water, the mixture was diluted with dichloromethane, washed with water, dried and evaporated. Purification on silica after elution with ethyl acetate/heptane 1:1 yielded 12.0 g (86%) 1-[2-(4-allyloxy-benzylsulfanyl)-ethyl]-1H[1,2,3]triazole as slightly yellow oil.

$^1$H-NMR (400 MHz, D$_6$-DMSO): δ=2.86 (t, 2H, SCH$_2$—CH$_2$-triazole), 3.65 (s, 2H, SCH$_2$Ph), 4.54 (m, 4H, CH$_2$-triazole, OCH$_2$-vinyl), 5.24 (d, 1H, =CH$_2$), 5.38 (d, 1H, =CH$_2$), 6.03 (m, 1H, CH=CH$_2$), 6.51 (d, 2H, 3-H/5-H), 6.99 (d, 2H, 2-H/6-H), 7.73 (s, 1H, triazole), 8.12 (s, 1H, triazole).

To a solution of 1.90 g (6.9 mmol) 1-[2-(4-all yloxy-benzylsulfanyl)-ethyl]-1H-[1,2,3]triazole in 150 ml dichloromethane was added dropwise at −30° C. a solution of 1.86 g (8.3 mmol) 3-chloro-benzenecarboperoxoic acid in 40 ml ethyl acetate and stirring continued for 1 hour. The mixture was allowed to warm up over night, washed with sodium bicarbonate and sodium carbonate solution, then with water, dried and evaporated. Elution form silica with ethyl acetate/methanol 5:1 furnished 1.25 g (62%) 1-[2-(4-allyloxy-phenylmethanesulfinyl)-ethyl]-1H-[1,2,3]triazole as white solid.

$^1$H-NMR (400 MHz, D$_6$-DMSO): δ=3.11 (m, 1H, CH$_2$—CH$_2$-triazole), 3.32 (m, 1H, CH$_2$—CH$_2$-triazole), 3.94 (d, 1H, SCH$_2$Ph), 4.12 (d, 1H, SCH$_2$Ph), 4.56 (m, 2H, CH$_2$-triazole), 4.56 (m, 2H, OCH$_2$-vinyl), 5.25 (d, 1H, =CH$_2$), 5.38 (d, 1H, =CH$_2$), 6.03 (m, 1H, CH=CH$_2$), 6.94 (d, 2H, 3-H/5-H), 7.22 (d, 2H, 2-H/6-H), 7.74 (s, 1H, triazole), 8.16 (s, 1H, triazole).

To a solution of 28.46 g (0.182 mol) 1,3-dimethyl-pyrimidine-2,4,6-trione and 1.81 g (1.57 mmol) tetrakis-(triphenylphosphine)-palladium in 600 ml dichloromethane was added dropwise a solution of 17.70 g (60.75 mmol) 1-[2-(4-allyloxy-phenylmethanesulfinyl)-ethyl]-1H-[1,2,3] triazole and stirring was continued for 6 hours at 45° C. It was allowed to cool down over night. The reaction mixture was extracted with three portions of sodium bicarbonate solution, then the aqueous phase was adjusted to pH 1 and extracted three times with ethyl acetate. The organic extract was dried and evaporated to yield 12.6 g (83%) 4-(2[1,2,3]triazol-1-yl-ethanesulfinylmethyl)-phenol as white solid.

$^1$H-NMR (400 MHz, D$_6$-DMSO): δ=3.10 (dt, 1H, CH$_2$—CH$_2$-triazole), 3.29 (dt, 1H, CH$_2$—CH$_2$-triazole), 3.90 (d, 1H, SCH$_2$Ph), 4.06 (d, 1H, SCH$_2$Ph), 4.78 (m, 2H, CH$_2$-triazole), 6.75 (d, 2H, 3-H/5-H), 7.11 (d, 2H, 2-H/6-H), 7.75 (s, 1H, triazole), 8.17 (s, 1H, triazole), 9.50 (s, 1H, OH).

To a solution of 17.0 g (109 mmol) 1,3-dimethyl-pyrimidine-2,4,6-trione and 1.15 g (0.99 mmol) tetrakis-(triphenylphosphine)-palladium in 600 ml dichloromethane was added dropwise a solution of 10.0 g (36.3 mmol) 1-[2-(4-allyloxy-benzylsulfanyl)-ethyl]-1H-[1,2,3]triazole in 200 ml dichloromethane and stirring was continued for 5 hours at 45° C. It was allowed to cool down over night. The reaction mixture was washed thrice with 500 ml sodium bicarbonate solution, 500 ml water, then the aqueous phase was extracted with 200 ml dichloromethane. The combined organic phases were dried, evaporated and purified by chromatography on silica (ethyl acetate/n-heptane 3:1) to yield 5.78 g (68%) 4-(2-[1,2,3]triazol-1-yl-ethanesulfanylmethyl)-phenol as white solid.

$^1$H-NMR (400 MHz, D$_6$-DMSO): δ=2.85 (t, 2H, SCH$_2$—CH$_2$-triazole), 3.60 (s, 2H, SCH$_2$Ph), 4.53 (t, 2H, CH$_2$-triazole), 6.70 (d, 2H, 3-H/5-H), 7.10 (d, 2H, 2-H/6-H), 7.73 (s, 1H, triazole), 8.11 (s, 1H, triazole), 9.35 (s, 1H, OH).

A mixture of 0.158 g (0.63 mmol) 4-(2-[1,2,3]triazol-1-yl-ethanesulfinylmethyl)-phenol and 0.124 g (0.38 mmol) cesium carbonate in 10 ml butanone was stirred at 60° C. for 30 min, then 0.25 g (0.63 mmol) 4-chloromethyl-2-[2-(4-trifluoromethyl-sulfanyl-phenyl)-vinyl]oxazole and 0.105 g (0.63 mmol) potassium iodide were added and stirring at 60° C. continued for 2 days. After removal of solvent and partitioning of the residue between ethyl acetate and water, the organic phase was washed with 1 N NaOH and dried over sodium sulfate. The solution was concentrated and purified on silica. Elution with ethyl acetate/methanol 9:1 yielded 0.081 g (24%)1-[4-(4-{2-[2-(4-trifluoromethylsulfanyl-phenyl)-vinyl]-oxazol-4-ylmethoxy}-phenylmethanesulfinyl)-ethyl]-1H-[1,2,3]triazole as white solid melting at 182–184° C.

MS: M=534.9 (ESI+) $^1$H-NMR (400 MHz, D$_6$-DMSO): δ=3.13 (dt, 1H, CH$_2$—CH2-N), 3.35 (dt, 1H, CH$_2$-13 CH$_2$-N), 3.96 (d, 1H, CH$_2$—Ar), 4.14 (d, 1H, CH$_2$—Ar), 4.79 (m, 2H, CH$_2$-triazole), 5.04 (s, 2H, OCH$_2$-oxazole), 7.05 (d, 2H, 3'-,5'-H), 7.26 (d, 2H, 2'-,6'-H), 7.31 (d, 1H, =CH), 7.59 (d, 1H, =CH), 7.74 (d, 2H, Ar—SCF₃), 7.75 (s, 1H, triazole), 7.88 (d, 2H, Ar—SCF₃), 8.17 (s, 1H, triazole), 8.26 (s, 1H, oxazole).

Example 5

1-[2-(4-{2-[2-(E)-(4-Difluoromethoxy-phenyl)-vinyl]-oxazol-4-ylmethoxy}-phenylmethanesulfinyl)-ethyl]-1H-[1,2,3]triazole A mixture of 10.0 g (7.68 ml, 58.1 mmol) 4-difluoromethoxy-benzaldehyde, 6.65 g (63.9 mmol) malonic acid, 0.21 g (2.50 mmol) piperidine and 50 ml pyridine was kept at reflux temperature until carbon dioxide development ceased (3 h). After cooling to room temperature the reaction mixture was poured onto 200 g ice and 100 ml 6N HCl. The precipitate was isolated, washed with water and dried. Yield: 8.8 g (71%) 3-(4-Difluoromethoxy-phenyl)-acrylic acid.

¹H-NMR (400 MHz, D₆-DMSO): δ=6.51 (d, 1H, 2-H), 7.21 (d, 2H, 3'-/5'-H), 7.32 (t, 1H, OCHF₂), 7.59 (d, 1H, 3-H), 7.77 (d, 2H, 2'-/6'-H), 12.4 (br, 1H, COOH)

To a suspension of 8.70 g (40.6 mmol) 3-(4-difluoromethoxy-phenyl)-acrylic acid in 60.0 ml tetrahydrofuran and 0.6 ml N,N-dimethylformamide a solution of 5.14 ml (60.9 mmol) oxalyl chloride in 10 ml tetrahydrofuran was added dropwise at 0° C. within 10 min. Stirring was continued at 0–5° C. for 30 min. and 2 h at room temperature thereafter. The resulting solution was cooled to 0–5° C. again and then added within 15 min. to 150 ml of a 25% aqueous ammonia solution. The separating oil was collected and stirred for 30 min. with water. The precipitated amide was collected, washed with water and dried at 40° C. in vacuo. Yield: 4.7 g (54%) 3-(4-Difluoromethoxy-phenyl)-acrylamide.

MS: M=214.2 (API+). ¹H-NMR (400 MHz, D₆-DMSO): δ=6.57 (d, 1H, 2-H), 7.10 (br, 1H, NH), 7.21 (d, 2H, 3'-/5'-H), 7.29 (t, 1H, CHF₂), 7.45 (d, 1H, 3-H), 7.53 (br, 1H, NH), 7.63 (d, 2H, 2'-/6'-H).

4.50 g (21.1 mmol) 3-(4-Difluoromethoxy-phenyl)-acrylamide, 3.20 g (25.2 mmol) dichloroacetone and 45 ml toluene were kept at reflux temperature for 22 h with continuous removal of water by use of a water separator (Dean-Stark trap). After removal of solvents in vacuo, the residue was stirred with diethyl ether, the precipitate (some remaining starting material) sucked off and the filtrate evaporated to dryness. The residue was extracted three times with heptane, the heptane fractions evaporated and the residue dried in vacuo. Yield: 1.0 g (16%) 4-Chloromethyl-2-[2-(4-difluoromethoxy-phenyl)-vinyl]-oxazole.

MS: M=286.2 (API+) ¹H-NMR (400 MHz, D₆-DMSO): δ=4.70 (s, 2H, CH₂Cl, 7.14 (d, 1H, =CH), 7.22 (d, 2H, Ar—H), 7.31 (t, 1H, OCHF₂), 7.54 (d, 1H, =CH), 7.80 (d, 2H, Ar—H), 8.17 (s, 1H, oxazole).

A solution of 126 mg (0.50 mmol) 4-(2-[1,2,3]triazol-1-yl-ethanesulfinylmethyl)-phenol in 4 ml N,N-dimethylformamide was treated at 0° C. with 14 mg (0.55 mmol) sodium hydride and stirred at that temperature for 30 min, then 143 mg (0.50 mmol) 4-chloromethyl-2-[2-(4-difluoromethoxy-phenyl)-vinyl]-oxazole were added and stirring continued over night at room temperature. After addition of 8 ml water, the precipitate was isolated, washed thoroughly with water, and purified on silica. Elution with ethyl acetate/methanol (0 to 20%) yielded 123 mg (33%) 1-[2-(4-{2-[2-(E)-(4-difluoromethoxy-phenyl)-vinyl]-oxazol-4-ylmethoxy}-phenylmethanesulfinyl)-ethyl]-1H-[1,2,3]triazole as beige solid.

MS: M=501.4 (ESI+) ¹H-NMR (400 MHz, D₆-DMSO): δ=3.12 (dt, 1H, C$\underline{H}_2$—CH₂-N), 3.34 (dt, 1H, C$\underline{H}_2$—CH2-N), 3.96 (d, 1H, CH₂—Ar), 4.13 (d, 1H, CH₂—Ar), 4.79 (m, 2H, CH₂-triazole), 5.02 (s, 2H, OCH₂-oxazole), 7.05 (d, 2H, 3'-,5'-H), 7.15 (d, 1H, =CH), 7.21 (d, 2H, 2'-,6'-H), 7.25 (d, 2H, Ar—OCHF₂), 7.40 (d, 1H, CHF₂), 7.53 (d, 1H, =CH), 7.75 (s, 1H, triazole), 7.80 (d, 2H, Ar—OCHF₂), 8.17 (s, 1H, triazole), 8.21 (s, 1H, oxazole).

Example 6

1-[2-(4-{2-[2-(4-Trifluoromethyl-phenyl)-vinyl]-oxazol-4-ylmethoxy}-benzylsulfanyl)-ethyl]-1H-[1,2,3]triazole A solution of 150 mg (0.64 mmol) 4-(2-[1,2,3]triazol-1-yl-ethanesulfanylmethyl)-phenol in 4 ml N,N-dimethylformamide was treated with 18 mg (0.64 mmol) sodium hydride and stirred at room temperature for 15 min, then 184 mg (0.64 mmol) 4-chloromethyl-2-[2-(4-trifluoromethyl-phenyl)-vinyl]-oxazole were added and stirring continued over night. After addition of 13 ml water, the precipitate was isolated, washed thoroughly with water, diluted methanol, and ether, and dried in vacuo at 40° C. Yield: 210 mg (67%) 1-[2-(4-{2-[2-(E)-(4-Trifluoromethyl-phenyl)-vinyl]-oxazol-4-ylmethoxy}-benzylsulfanyl)-ethyl]-1H-[1,2,3]triazole.

¹H-NMR (400 MHz, D₆-DMSO): δ=2.87 (t, 2H, C$\underline{H}_2$—CH2-N), 3.66 (s, 2H, CH₂—Ph), 4.55 (t, 2H, CH₂-triazole), 5.02 (s, 2H, OCH₂-oxazole), 7.00 (d, 2H, 3'-,5'-H), 7.25 (d, 2H, 2'-,6'-H), 7.33 (d, 1H, =CH), 7.62 (d, 1H, =CH), 7.73 (s, 1H, triazole), 7.76 (d, 2H, Ar—CF₃), 7.95 (d, 2H, Ar—CF₃), 8.12 (s, 1H, triazole), 8.25 (s, 1H, 5-H-oxazole).

Example 7

1-[2-(4-{2-[2-(E)-(2-Fluoro-4-trifluoromethyl-phenyl)-vinyl]-oxazol-4-ylmethoxy}-benzylsulfanyl)-ethyl]-1H-[1,2,3]triazole A mixture of 5.0 g (3.55 ml, 26.0 mmol) 2-fluoro-4-trifluoromethyl-benzaldehyde, 3.10 g (29.8 mmol) malonic acid, 0.26 g (0.30 ml, 3.0 mmol) piperidine and 15 ml pyridine was kept at reflux temperature until carbon dioxide development ceased (3 h). After cooling to room temperature the reaction mixture was poured onto 300 g ice and 100 ml 6N HCl. The precipitate was isolated, washed with water, twice with n-heptane and dried. Yield: 5.2 g (85%) 3-(2-Fluoro-4-trifluoromethyl-phenyl)-acrylic acid.

¹H-NMR (400 MHz, D₆-DMSO): δ=6.73 (d, J=16.1 Hz, 1H, 2-H), 7.63 (d, 1H, 5'-H), 7.65 (d, J=16.1 Hz, 1H, 3-H), 7.76 (d, 1H, 3'-H), 8.07 (dd, 1H, 6'-H), 12.8 (br, 1H, COOH).

To a suspension of 5.00 g (21.4 mmol) 3-(2-fluoro-4-trifluoromethyl-phenyl)-acrylic acid in 30.0 ml tetrahydrofuran and 0.2 ml N,N-dimethylformamide a solution of 3.60 ml (28.0 mmol) oxalyl chloride in 10 ml tetrahydrofuran was added in drops at 0° C. within 10 min. Stirring was continued at 0–5° C. for 30 min. and 2 h at room temperature thereafter. The resulting solution was cooled to 0–5° C. again and then added within 15 min. to 150 ml of a 25% aqueous ammonia solution. The separating oily amide was collected and stirred for 30 min. with water. The precipitate was collected, washed with water and dried at 40° C. in vacuo. Yield: 4.4 g (88%) 3-(2-Fluoro-4-trifluoromethyl-phenyl)-acrylamide.

MS: M=234.2 (API+). $^1$H-NMR (400 MHz, D$_6$-DMSO): δ=6.83 (d, 1H, 2-H), 7.31 (br, 1H, NH), 7.51 (d, 1H, 3-H), 7.63 (d, 1H, 5'-H), 7.70 (d, 1H, 3'-H), 7.76(br, 1H, NH), 7.89 (dd, 1H, 6'-H).

4.00 g (17.1 mmol) 3-(2-Fluoro-4-trifluoromethyl-phenyl)-acrylamide, 2.60 g (21.3 mmol) 1,3-dichloroacetone and 40 ml toluene were kept at reflux temperature for 16 h with continuous removal of water by use of a water separator (Dean-Stark trap). After cooling to room temperature, two extractions with 100 ml water were performed, the organic phase was dried over sodium sulphate and the solvent removed in vacuo. Chromatography on silica gel (eluent: n-heptane/ethyl acetate 5:1) gave 1.20 g (23%) 4-chloromethyl-2-[2-(2-fluoro-4-trifluoromethyl-phenyl)-vinyl]-oxazole.

MS: M=306.2 (API+) $^1$H-NMR (400 MHz, D$_6$-DMSO): δ=4.71 (s, 2H, CH$_2$Cl, 7.38 (d, J=16.4 Hz, 1H, 1'-H), 7.60 (d, J=16.4 Hz, 1H, 2'-H), 7.63 (d, 1H, 5"-H), 7.76 (d, 1H, 3"-H), 8.14 (dd, 1H, 6"-H), 8.23 (s, 1H, 5-H-oxazole).

A solution of 294 mg (1.25 mmol) 4-(2-[1,2,3]triazol-1-yl-ethanesulfanylmethyl)-phenol in 7 ml N,N-dimethylformamide was treated with 32 mg (1.25 mmol) sodium hydride and stirred at room temperature for 15 min, then 385 mg (1.25 mmol) 4-chloromethyl-2-[2-(2-fluoro-4-trifluoromethyl-phenyl)-vinyl]-oxazole were added and stirring continued for 65 hours. After addition of 25 ml water, the precipitate was isolated, washed thoroughly with water, water/methanol 1:1, and heptane/ethyl acetate 1:3, and dried in vacuo at 40° C. Yield: 443 mg (70%) 1-[2-(4-{2-[2-(E)-(2-Fluoro-4-trifluoromethyl-phenyl)-vinyl]-oxazol-4-ylmethoxy}-benzylsulfanyl)-ethyl]-1H-[1,2,3]triazole.

MS: M=505.4 (API+). $^1$H-NMR (400 MHz, D$_6$-DMSO): δ=2.87 (t, 2H, CH$_2$—CH2-N), 3.67 (s, 2H, CH$_2$—Ph), 4.55 (t, 2H, CH$_2$-triazole), 5.03 (s, 2H, OCH$_2$-oxazole), 6.99 (d, 2H, 3'-,5'-H), 7.25 (d, 2H, 2'-,6'-H), 7.39 (d, 1H, =CH), 7.59 (d, 1H, =CH), 7.64 (d, 1H, 5"-H), 7.73 (s, 1H, triazole), 7.78 (d, 1H, 3"-H), 8.12 (s, 1H, triazole), 8.16 (dd, 1H, 6"-H), 8.28(s, 1H, 5-H-oxazole).

Example 8

1-[2-(4-{2-[2-(4-Chloro-phenyl)-vinyl]-oxazol-4-ylmethoxy}-benzylsulfanyl)-ethyl]-1H-[1,2,3]triazole A solution of 294 mg (1.25 mmol) 4-(2-[1,2,3]triazol-1-yl-ethanesulfanylmethyl)-phenol in 7 ml N,N-dimethylformamide was treated with 32 mg (1.25 mmol) sodium hydride and stirred at room temperature for 15 min, then 318 mg (1.25 mmol) 4-chloromethyl-2-[2-(4-chloro-phenyl)-vinyl]-oxazole were added and stirring continued over night. After addition of 20 ml water, the precipitate was isolated, washed thoroughly with water, hot methanol, and ether, and dried in vacuo at 40° C. Yield: 455 mg (80%) 1-[2-(4-{2-[2-(E)-(4-Chloro-phenyl)vinyl]-oxazol-4-ylmethoxy}-benzylsulfanyl)-ethyl]-1H-[1,2,3]triazole as off-white solid.

$^1$H-NMR (400 MHz, D$_6$-DMSO): δ=2.87 (t, 2H, CH$_2$—CH$_2$-N), 3.66 (s, 2H, CH$_2$-Ph), 4.55 (t, 2H, CH$_2$-triazole), 5.00 (s, 2H, OCH$_2$-oxazole), 6.99, 2H, 3'-,5'-H), 7.19 (d, 1H, =CH), 7.25 (d, 2H, 2'-,6'-H), 7.47 (d, 2H, Ar—H), 7.53 (d, 1H, =CH), 7.73 (s, 1H, triazole), 7.76 (d, 2H, Ar—H), 8.12 (s, 1H, triazole), 8.21 (s, 1H, 5-H-oxazole).

Example 9

1-[2-(4-{2-[2-(E)-(4-Chloro-2-fluoro-phenyl)-vinyl]-oxazol-4-ylmethoxy}-benzylsulfanyl)-ethyl]-1H-[1,2,3]triazole To a suspension of 49.0 g (244 mmol) 3-(4-chloro-2-fluoro-phenyl)-acrylic acid in 300 ml tetrahydrofuran and 2.8 ml N,N-dimethylformamide a solution of 26.2 ml (305 mmol) oxalyl chloride in 50 ml tetrahydrofuran was added dropwise at 0° C. within 45 min. Stirring was continued at 0–5° C. for 30 min. and 2 h at room temperature thereafter. The resulting solution was cooled to 0–5° C. again and then added within 15 min. to 750 ml of a 25% aqueous ammonia solution. Tetrahydrofuran was distilled off in vacuo, precipitated amide was collected, washed with water and heptane, then dried at 40° C. in vacuo. Yield: 45.9 g (94%) 3-(4-Chloro-2-fluoro-phenyl)-acrylamide.

$^1$H-NMR (400 MHz, D$_6$-DMSO): δ=6.72 (d, 1H, 2-H), 7.23 (br, 1H, NH), 7.35 (d, 1H, 5'-H), 7.44 (d, 1H, 3-H), 7.50 (d, 1H, 3'-H), 7.68 (br, 1H, NH), 7.95 (dd, 1H, 6'-H).

45.0 g (225 mmol) 3-(4-Chloro-2-fluoro-phenyl)-acrylamide, 35.5 g (280 mmol) 1,3-dichloroacetone and 500 ml toluene were kept at reflux temperature for 24 h with continuous removal of water by use of a water separator (Dean-Stark trap). After cooling to room temperature, two extractions with 80 ml water, the organic phase was dried over sodium sulphate and the solvent removed in vacuo. The residue was stirred with 80 ml methanol for 30 min., the precipitate filtered, washed with cold methanol, stirred with n-heptane, sucked off and dried in vacuo at 40° C. Yield: 28.9 g (47%) 2-[2-(4-Chloro-2-fluoro-phenyl)-vinyl]-4-chloromethyl-oxazole.

$^1$H-NMR (400 MHz, D$_6$-DMSO): δ=6.72 (d, 1H, 1'-H), 7.35 (d, 1H, 5"-H), 7.44 (d, 1H, 2'-H), 7.50 (d, 1H, 3"-H), 7.95 (dd, 1H, 6"-H), 8.21 (s, 1H, 5-H-oxazole).

A solution of 294 mg (1.25 mmol) 4-(2-[1,2,3]triazol-1-yl-ethanesulfanylmethyl)-phenol in 7 ml N,N-dimethylformamide was treated with 32 mg (1.25 mmol) sodium hydride and stirred at room temperature for 15 min, then 385 mg (1.25 mmol) 4-chloromethyl-2-[2-(4-chloro-2-fluoro-phenyl)-vinyl]-oxazole were added and stirring continued for 18 hours. After addition of 20 ml water, the precipitate was isolated, washed thoroughly with water, water/methanol 1:1, and heptane/ethyl acetate 1:2, and dried in vacuo at 40° C. Yield: 366 mg (62%) 1-[2-(4-{2-[2-(E)-(4-Chloro-2-fluoro-phenyl)-vinyl]-oxazol-4-ylmethoxy}-benzyl-sulfanyl)-ethyl]-1H-[1,2,3]triazole.

$^1$H-NMR (400 MHz, D$_6$-DMSO): δ=2.87 (t, 2H, CH$_2$—CH$_2$-N), 3.66 (s, 2H, CH$_2$—Ph), 4.55 (t, 2H, CH$_2$-triazole), 5.01 (s, 2H, OCH$_2$-oxazole), 6.99 (d, 2H, 3'-,5'-H), 7.25 (d, 2H, 2'-,6'-H), 7.26 (d, 1H, 5"-H), 7.37 (d, 1H, =CH), 7.51 (d, 1H, =CH), 7.53 (d, 1H, 3"-H), 7.73 (s, 1H, triazole), 7.95 (dd, 1H, 6"-H), 8.12 (s, 1H, triazole), 8.24 (s, 1H, 5-H-oxazole).

Example 10

1-[2-(4-{2-[2-(E)-(2-Fluoro-4-trifluoromethyl-phenyl)-vinyl]-oxazol-4-ylmethoxy}-phenylmethanesulfonyl)-ethyl]-1H-[1,2,3]triazole To a solution of 101 mg (0.20 mmol) 1-[2-(4-{2-[2-(E)-(2-fluoro-4-trifluoromethylphenyl)-vinyl]-oxazol-4-yl-methoxy}-benzylsulfanyl)-ethyl]-1H-[1,2,3]triazole in 8 ml methanol were added dropwise during 20 min 492 mg (0.80 mmol) oxone dissolved in 4 ml water. After 24 hours stirring at room temperature the precipitate was isolated, dissolved in dichloromethane, washed with sodium bicarbonate solution, dried and evaporated. Elution from silica with ethyl acetate/methanol 25:1 furnished 57 mg (53%) title compound as white solid.

MS: M=537.3 (API+). $^1$H-NMR (400 MHz, D$_6$-DMSO): δ=3.70 (t, 2H, C$\underline{H}_2$—CH2-N), 4.43 (s, 2H, CH$_2$—Ph), 4.81 (t, 2H, CH$_2$-triazole), 5.06 (s, 2H, OCH$_2$-oxazole), 7.08 (d, 2H, 3'-,5'-H), 7.32 (d, 2H, 2'-,6'-H), 7.40 (d, 1H, =CH), 7.60 (d, 1H, =CH), 7.65 (d, 1H, 5"-H), 7.75 (s, 1H, triazole), 7.78 (d, 1H, 3"-H), 8.16 (dd, 1H, 6"-H), 8.18 (s, 1H, triazole), 8.30 (s, 1H, 5-H-oxazole).

Example 11

1-[2-(4-{2-[2-(E)-(2-Fluoro-4-trifluoromethyl-phenyl)-vinyl]-oxazol-4-ylmethoxy}-phenylmethanesulfinyl)-ethyl]-1H-[1,2,3]triazole To a solution of 101 mg (0.20 mmol) 1-[2-(4-{2-[2-(E)-(2-fluoro-4-trifluoromethylphenyl)-vinyl]-oxazol-4-ylmethoxy}-benzylsulfanyl)-ethyl]-1H-[1,2,3]triazole in 8 ml dichloromethane at −30° C. were added drop by drop during 20 min 54 mg (0.24 mmol) 3-chloro-benzenecarboperoxoic acid dissolved in 2 ml ethyl acetate. After 1 hour stirring at 30° C. the mixture was allowed to warm up over night, diluted with dichloromethane, washed with sodium bicarbonate solution, then with water, dried and evaporated. Elution from silica with ethyl acetate/methanol 9:1 furnished 73 mg (71%) title compound as white solid.

MS: M=521.3 (API+). $^1$H-NMR (400 MHz, D$_6$-DMSO): δ=3.12 (dt, 1H, C$\underline{H}_2$—CH2-N), 3.34 (dt, 1H, C$\underline{H}_2$—CH2-N), 3.96 (d, 1H, CH$_2$—Ph), 4.14 (d, 1H, CH$_2$—Ph), 4.79 (m, 2H, CH$_2$-triazole), 5.05 (s, 2H, OCH$_2$-oxazole), 7.05 (d, 2H, 3'-,5'-H), 7.25 (d, 2H, 2'-,6'-H), 7.40 (d, 1H, =CH), 7.60 (d, 1H, =CH), 7.65 (d, 1H, 5"-H), 7.75 (s, 1H, triazole), 7.78 (d, 1H, 3"-H), 8.17 (dd, 1H, 6"-H), 8.18 (s, 1H, triazole), 8.29 (s, 1H, 5-H-oxazole).

Example 12

1-[2-(4-{2-[2-(E)-(4-Chloro-2-fluoro-phenyl)-vinyl]-oxazol-4-ylmethoxy}-phenylmethanesulfinyl)-ethyl]-1H-[1,2,3]triazole To a solution of 320 mg (0.68 mmol) 1-[2-(4-{2-[2-(E)-(4-chloro-2-fluoro-phenyl)vinyl]-oxazol-4-ylmethoxy}-benzylsulfanyl)-ethyl]-1H-[1,2,3]triazole in 9 ml dichloromethane at −30° C. were added dropwise during 20 min 197 mg (0.88 mmol) 3-chloro-benzenecarboperoxoic acid dissolved in 9 ml ethyl acetate. After 1 hour stirring at 30° C. the mixture was allowed to warm up over night, stirred another 48 hours at room temperature, diluted with dichloromethane, washed with sodium bicarbonate solution, then with water, dried and evaporated. Elution from silica with ethyl acetate/methanol 20:1 furnished as the second fraction 171 mg (51%) title compound as white solid.

MS: M=486.8 (ESI+). $^1$H-NMR (400 MHz, D$_6$-DMSO): δ=3.12 (quintet, 1H, C$\underline{H}_2$—CH2-N), 3.34 (quintet, 1H, C$\underline{H}_2$—CH2-N), 3.96 (d, 1H, CH$_2$—Ph), 4.13 (d, 1H, CH$_2$—Ph), 4.78 (quintet, 2H, CH$_2$-triazole), 5.03 (s, 2H, OCH$_2$-oxazole), 7.05 (d, 2H, 3'-,5'-H), 7.25 (d, 2H, 2'-,6'-H), 7.27 (d, 1H, =CH), 7.36 (d, 1H, =CH), 7.54 (m, 2H), 7.75 (s, 1H, triazole), 7.96 (dd, 1H, 6"-H), 8.17 (s, 1H, triazole), 8.25 (s, 1H, 5-H-oxazole).

Example 13

1-[2-(4-{2-[2-(E)-(4-Chloro-2-fluoro-phenyl)-vinyl]-oxazol-4-ylmethoxy}-phenylmethanesulfonyl)-ethyl]-1H-[1,2,3]triazole The first fraction from the chromatography of example 12 consisted of 96 mg (28%) title compound as white solid.

MS: M=502.8 (ESI+). $^1$H-NMR (400 MHz, D$_6$-DMSO): δ=3.70 (t, 2H, CH2—CH2-N), 4.43 (s, 2H, CH2-Ph), 4.81 (t, 2H, CH2-triazole), 5.04 (s, 2H, OCH2-oxazole), 7.08 (d, 2H, 3'-,5'-H), 7.26 (d, 1H, =CH), 7.32 (d, 2H, 2'-,6'-H), 7.36 (d, 1H, 5"-H), 7.52 (d, 1H, =CH), 7.55 (d, 1H, 3"-H), 7.75 (s, 1H, triazole), 7.94 (dd, 1H, 6"-H), 8.18 (s, 1H, triazole), 8.26 (s, 1H, 5-H-oxazole)

Example 14

1-[2-(2-Methyl-4-{2-[2-(4-trifluoromethoxy-phenyl)-vinyl]-oxazol-4-ylmethoxy}-benzylsulfanyl)-ethyl]-1H-[1,2,3]triazole 31.7 g (229 mmol) potassium carbonate and 9.51 g (57.3 mmol) potassium iodide were given to a solution of 15.6 g (115 mmol) 4-hydroxy-2-methyl-benzaldehyde and 55.4 g (458 mmol) allyl bromide in 500 ml 2-butanone and stirred for 16 h at 65° C. Solvents were distilled off and the residue distributed between ethyl acetate and 1 N sodium hydroxide. The organic layer was separated and the aqueous solution extracted once with ethyl acetate. The combined organic phases were dried and evaporated to give 19.8 g (98%) of 4-allyloxy-2-methyl-benzaldehyde.

$^1$H-NMR (400 MHz, D$_6$-DMSO): δ=2.59 (s, 3H, CH$_3$), 4.67 (d, 2H, OC$\underline{H}_2$-vinyl), 5.29 (d, 1H, =CH$_2$), 5.41 (d, 1H, =CH$_2$), 6.05 (m, 1H, C$\underline{H}$=CH$_2$), 6.96 (d, 1H, 5-H), 6.74 (s, 1H, 3-H), 7.77 (d, 1H, 6-H), 10.07 (s, 1H, CHO).

8.50 g (224 mmol) lithium aluminium hydride were given to 250 ml Tetrahydrofuran (THF) and stirred for 20 min. A solution of 19.4 g (110 mmol) 4-allyloxy-2-methyl-benzaldehyde in 100 ml THF was added dropwise and stirring continued for 3 h. The reaction mixture was cooled to 0° C., carefully hydrolysed with 40 ml concentrated ammonium chloride solution, stirred for 60 min. and adjusted to pH=5 with conc. hydrochloric acid. A formed salt precipitate was removed by filtration, washed with THF and the combined organic solutions evaporated. Chromatography of the residue on silica (n-heptane/ethyl acetate 1:3) gave 16.0 g (81%) (4-allyloxy-2-methyl-phenyl)-methanol as a slightly yellow oil.

$^1$H-NMR (400 MHz, D$_6$-DMSO): δ=2.23 (s, 3H, CH$_3$), 4.40 (s, 2H, C$\underline{H}_2$OH), 4.52 (d, 2H, OC$\underline{H}_2$-vinyl), 4.88 (t, 1H, OH), 5.23 (d, 1H, =CH$_2$), 5.37 (d, 1H, =CH$_2$), 6.03 (m, 1H, C$\underline{H}$=CH$_2$), 6.72 (d, 1H, 5-H), 6.74 (s, 1H, 3-H), 7.20 (d, 1H, 6-H).

A solution of 16.0 g (89.6 mmol) (4-allyloxy-2-methyl-phenyl)-methanol in 270 ml dichloromethane and 1.5 ml DMF was cooled to 0° C. 7.80 ml (12.8 g, 108 mmol) thionyl chloride were added slowly and then stirred for 1 h at room temperature. Dichloromethane was distilled off, 300 ml toluene added and solvents removed in vacuo. The residue was taken up in 200 ml toluene and washed with concentrated sodium carbonate solution. The organic phase was dried and evaporated to give 17.5 g (99%) 1-allyloxy-4-chloromethyl-2-methyl-benzene as colored oil.

$^1$H-NMR (400 MHz, D$_6$-DMSO): δ=2.34 (s, 3H, CH$_3$), 4.55 (d, 2H, OC$\underline{H}_2$-vinyl), 4.55 (s, 2H, CH$_2$Cl), 5.25 (d, 1H, =CH$_2$), 5.38 (d, 1H, =CH$_2$), 6.02 (m, 1H, CH=CH$_2$), 6.75 (d, 1H, 5-H), 6.82 (s, 1H, 3-H), 7.29 (d, 1H, 6-H).

A mixture of 3.40 g (17.3 mmol) 1-allyloxy-4-chloromethyl-2-methyl-benzene and 1.45 g (19.0 mmol) thiourea in 5.0 ml ethanol was heated to reflux for 7 h. Solvents were distilled off and the crystalline residue was washed with cold ethanol and isolated by filtration. After addition of 5.0 ml ethanol, 2.0 ml water and 1.4 ml 25% aqueous ammonia, the mixture was heated to reflux for 2 h. Ethanol was distilled off, then acidified with 0.5 ml half conc. HCl and extracted with ethyl acetate. The solution was dried over MgSO$_4$ and solvents were removed in vacuum to yield 1.99 g (59%) (4-allyloxy-2-methyl-phenyl)-methanethiol as nearly colourless oil, which was used immediately.

$^1$H-NMR (400 MHz, D$_6$-DMSO): δ=2.30 (s, 3H, CH$_3$), 2.60 (br, 1H, SH), 3.67 (s, 2H, CH$_2$SH), 4.52 (d, 2H, OCH$_2$-vinyl), 5.24 (d, 1H, =CH$_2$), 5.36 (d, 1H, =CH$_2$), 6.03 (m, 1H, CH=CH$_2$), 6.71 (d, 1H, 5-H), 6.76 (s, 1H, 3-H), 7.15 (d, 1H, 6-H).

To a mixture of 1.98 g (10.2 mmol) (4-allyloxy-2-methyl-phenyl)-methanethiol and 2.72 g (10.2 mmol) toluene-4-sulfonic acid 2-[1,2,3]triazol-1-yl-ethyl ester in 25 ml N,N-dimethylformamide was added under argon at −50° C. 515 mg (20.4 mmol) sodium hydride. The mixture was allowed to warm up to room temperature and was stirred under argon for 12 hours. 80% of the DMF was stilled off in vacuo, ethyl acetate and water given to the mixture. The aqueous phase was reextracted with ethyl acetate and the combined organic extracts dried and evaporated to yield 2.8 g of 1-[2-(4-allyloxy-2-methyl-benzylsulfanyl)ethyl]-1H-[1,2,3]triazole as brown oil. The raw material (73% purity) was used without further purification.

To a solution of 4.65 g (29.8 mmol) 1,3-dimethyl-pyrimidine-2,4,6-trione and 347 mg (0.3 mmol) tetrakis-(triphenylphosphine)-palladium in 30 ml dichloromethane was added dropwise a solution of 2.78 g (9.61 mmol) 1-[2-(4-allyloxy-2-methyl-benzylsulfanyl)-ethyl]-1H-[1,2,3]triazole in 20 ml dichloromethane and stirring was continued for 6 hours at 45° C. It was allowed to cool down over night. The reaction mixture was diluted with 50 ml dichloromethane, extracted with three 100 ml portions of sodium bicarbonate solution, then the aqueous phase was extracted twice with 100 ml dichloromethane. The organic extract was dried, evaporated and purified by chromatography on silica (ethyl acetate/n-heptane 2:1) to yield 1.76 g (73%) 3-methyl-4-(2-[1,2,3]triazol-1-yl-ethanesulfanylmethyl)-phenol as oil.

$^1$H-NMR (400 MHz, D$_6$-DMSO): δ=2.23 (s, 3H, CH$_3$), 2.90 (t, 2H, SCH$_2$—CH$_2$-triazole), 3.62 (s, 2H, SCH$_2$Ph), 4.54 (t, 2H, CH$_2$-triazole), 6.51 (d, 1H, 6-H), 6.57 (s, 1H, 2-H), 6.99 (d, 1H, 5H), 7.73 (s, 1H, triazole), 8.11 (s, 1H, triazole), 9.24 (s, 1H, OH).

A solution of 10 mg (0.04 mmol) 3-Methyl-4-(2-[1,2,3]triazol-1-yl-ethanesulfanylmethyl)-phenol in 1.5 ml N,N-dimethylformamide was treated with 2 mg (0.04 mmol) 60% sodium hydride and stirred at room temperature for 10 min, then 12 mg (0.04 mmol) 4-chloromethyl-2-[2-(4-trifluoromethoxy-phenyl)-vinyl]-oxazole were added and stirring continued for 2 h. After addition of water, the precipitate was isolated, washed thoroughly with water, and dried to give 1-[2-(2-Methyl-4-{2-[2-(E)-(4-trifluoromethoxy-phenyl)-vinyl]-oxazol-4-ylmethoxy}-benzylsulfanyl)-ethyl]-1H-[1,2,3]triazole.

MS: M=538.9(API+, M+Na$^+$).

Example 15

1-[2-(2-Methyl-4-{2-[2-(E)-(4-trifluoromethoxy-phenyl)-vinyl]-oxazol-4-ylmethoxy}-phenyl-methanesulfinyl)-ethyl]-1H-[1,2,3]triazole To a solution of 1.16 g (4.01 mmol) 1-[2-(4-allyloxy-2-methyl-benzylsulfanyl)-ethyl]-1H[1,2,3]triazole in 26 ml dichloromethane was added dropwise at −30° C. a solution of 896 mg (4.00 mmol) 77% 3-chloro-perbenzoic acid in 9 ml dichloromethane and stirring continued for 1 hour. The mixture was allowed to warm up over night, washed thrice with sodium bicarbonate solution, then with water, dried (sodium sulphate) and evaporated. The residue was stirred with stirred twice with 20 ml diethyl ether for 20 min., the precipitate filtered and dried at 40° C. in vacuum. 1.08 g (88%) 1-[2-(4-allyloxy-2-methyl-phenylmethanesulfinyl)-ethyl]-1H-[1,2,3]triazole as white solid.

MS: M=305.4 (ESI+, M+Na$^+$). $^1$H-NMR (400 MHz, D6-DMSO): δ=2.28 (s, 3H, CH3), 3.26 (dt, 1H, CH2—CH2-triazole), 3.41 (dt, 1H, CH2—CH2-triazole), 4.00 (d, 1H, SCH2Ph), 4.14 (d, 1H, SCH2Ph), 4.56 (m, 2H, OCH2-vinyl), 4.82 (m, 2H, CH2-triazole), 5.25 (d, 1H, =CH2), 5.38 (d, 1H, =CH2), 6.02 (m, 1H, CH=CH2), 6.77 (d, 1H, 5-H), 6.81 (s, 1H, 3-H), 7.15 (d, 1H, 6-H), 7.75 (s, 1H, triazole), 8.18 (s, 1H, triazole).

A mixture of 27.4 g (176 mmol) 1,3-dimethyl-pyrimidine-2,4,6-trione, 2.00 g (1.73 mmol) tetrakis-(triphenylphosphine)-palladium, 17.9 g (58.6 mmol) 1-[2-(4-allyloxy-2-methyl-phenylmethanesulfinyl)-ethyl]-1H-[1,2,3]triazole and 750 ml dichloromethane was stirred for 5 hours at 45° C. It was allowed to cool down over night. The formed precipitate was isolated by filtration, washed once with little dichloromethane and several times with diethyl ether. The diethyl ether filtrates were discarded and the solid dried at 40° C. in vacuum to give 5.5 g of product. The combined dichloromethane solutions (first filtrate and washing filtrate) were extracted twice with 120 ml 1 M HCl and once with 100 ml water. The combined water and HCl phases were extracted twice with 100 ml dichloromethane and the organic phase, which contained only barbituric acid discarded. The aqueous acidic layer was adjusted to pH=6.3 by 2 N NaOH and concentrated in vacuum to a third of the former volume. After saturation with solid sodium chloride, the mixture was extracted six times with 120 ml ethyl acetate. The combined organic layers were dried (sodium sulphate) and evaporated. The residue was stirred with ether, filtered and dried at 40° C. in vacuum to yield 6.3 g, total 11.8 g (76%) of 2-methyl-4-(2-[1,2,3]triazol-1-yl-ethane-sulfinylmethyl)-phenol.

MS: M=288.3 (ESI+, M+Na$^+$). $^1$H-NMR (400 MHz, D$_6$-DMSO): δ=2.22 (s, 3H, CH$_3$), 3.23 (dt, 1H, CH$_2$—CH$_2$-triazole), 3.39 (dt, 1H, CH$_2$—CH$_2$-triazole), 3.96 (d, 1H, SCH$_2$Ph), 4.08 (d, 1H, SCH$_2$Ph), 4.81 (m, 2H, CH$_2$-triazole), 6.56 (d, 1H, 5-H), 6.61 (s, 1H, 3-H), 7.02 (d, 1H, 6-H), 7.75 (s, 1H, triazole), 8.17 (s, 1H, triazole), 9.39 (s, 1H, OH).

A solution of 133 mg (0.50 mmol) 2-methyl-4-(2-[1,2,3]triazol-1-yl-ethanesulfinylmethyl)-phenol in 4 ml N,N-dimethylformamide was treated at 0° C. with 24 mg (0.60 mmol) 60% sodium hydride and stirred at that temperature for 30 min, then 152 mg (0.50 mmol) 4-chloromethyl-2-[2-(4-trifluoromethoxy-phenyl)-vinyl]-oxazole were added and stirring continued over night at room temperature. After addition of 8 ml water, the precipitate was isolated, washed thoroughly with water, methanol/water 1:1, ether and purified by chromatography on silica. Gradient elution with ethyl acetate (5 to 10% methanol) gave 65 mg (24%) 1-[2-(2-methyl-4-{2-[2-(E)-(4-trifluoromethoxy-phenyl)-vinyl]-oxazol-4-ylmethoxy}-phenyl-methanesulfinyl)-ethyl]-1H-[1,2,3]triazole as solid.

MS: M=533.5 (ESI+). $^1$H-NMR (400 MHz, D$_6$-DMSO): δ=2.30 (s, 3H, CH$_3$), 3.29 (dt, 1H, CH$_2$—CH2-N), 3.43 (dt, 1H, CH$_2$—CH2-N), 4.01 (d, 1H, CH$_2$—Ph), 4.15 (d, 1H, CH$_2$—Ph), 4.82 (m, 2H, CH$_2$-triazole), 5.01 (s, 2H, OCH$_2$-oxazole), 6.88 (d, 1H, 5-H, OPh), 6.91 (s, 1H, 3-H, OPh), 7.17 (d, 1H, 6-H, OPh), 7.21 (d, 1H, =CH), 7.40 (d, 2H, ArOCF$_3$), 7.56 (d, 1H, =CH), 7.75 (s, 1H, triazole), 7.87 (d, 2H, ArOCF3), 8.18 (s, 1H, triazole), 8.22 (s, 1H, 5-H-oxazole).

Example 16

1-[2-(2-Methyl-4-{2-[2-(E)-(4-trifluoromethoxy-phenyl)-vinyl]-oxazol-4-ylmethoxy}-phenyl-methanesulfonyl)-ethyl]-1H-[1,2,3]triazole 35 mg (0.15 mmol) 75% 3-chloroperoxybenzoic acid dissolved in 5 ml ethyl acetate were given at −30° C. to solution of 52 mg (0.10 mmol) 1-[2-(2-methyl-4-{2-[2-(E)-(4-trifluoromethoxy-phenyl)-vinyl]-oxazol-4-ylmethoxy}-phenyl-methanesulfinyl)-ethyl]-1H[1,2,3]triazole in 25 ml dichloromethane. The mixture was stirred for 48 h and slowly allowed to reach room temperature. Additional 20 ml dichloromethane were added, washed with conc. sodium carbonate solution, water, dried and evaporated to give 29 mg (53%) of the title compound.

MS: M=549.2 (ESI+). $^1$H-NMR (400 MHz, D$_6$-DMSO): δ=2.34 (s, 3H, CH$_3$), 3.83 (t, 2H, CH$_2$—CH2-N), 4.43 (d, H, CH$_2$—Ph), 4.86 (t, 2H, CH$_2$-triazole), 5.02 (s, 2H, OCH$_2$-oxazole), 6.90 (d, 1H, 5-H, OPh), 6.93 (s, 1H, 3-H, OPh), 7.21 (d, 1H, vinyl-H), 7.22 (d, 1H, 6-H, OPh), 7.40 (d, 2H, ArOCF$_3$), 7.57 (d, 1H, vinyl-H), 7.76 (s, 1H, triazole), 7.86 (d, 2H, ArOCF$_3$), 8.21 (s, 1H, triazole), 8.23 (s, 1H, 5-H-oxazole).

Example 17

1-[2-(4-{2-[(E)-2-(4-Chloro-2-fluoro-phenyl)-vinyl]-oxazol-4-ylmethoxy}-2-methyl-phenylmethanesulfanyl)-ethyl]-1H-[1,2,3]triazole A solution of 550 mg (2.21 mmol) 3-methyl-4-(2-[1,2,3]triazol-1-yl-ethanesulfanylmethyl)-phenol in 18.0 ml N,N-dimethylformamide was treated at 0° C. with 67 mg (2.6 mmol) sodium hydride and stirred at room temperature for 30 min., then 601 mg (2.21 mmol) 4-chloromethyl-2-[2-(2-fluoro-4-chloro-phenyl)-vinyl]-oxazole were added and stirring continued for 18 hours. After addition of 20 ml water, the precipitate was isolated, washed thoroughly with water, 2×10 ml methanol, heptane/ethyl acetate 1:2, and dried in vacuo at 40° C. Yield: 710 mg (66%) 1-[2-(2-methyl-4-{2-[2-(E)-(4-chloro-2-fluoro-phenyl)-vinyl]-oxazol-4-ylmethoxy}-benzylsulfanyl)-ethyl]-1H-[1,2,3]triazole. MS: M=485.4(ESI+).

Example 18

1-[2-(4-{2-[(E)-2-(4-Chloro-2-fluoro-phenyl)-vinyl]-oxazol-4-ylmethoxy}-2-methyl-phenylmethanesulfinyl)-ethyl]-1H-[1,2,3]triazole To a solution of 710 mg (1.46 mmol) 1-[2-(2-methyl-4-{2-[2-(E)-(4-chloro-2-fluorophenyl)-vinyl]-oxazol-4-yl-methoxy}-benzylsulfanyl)-ethyl]-1H-[1,2,3]triazole in 35 ml dichloromethane at −30° C. were added dropwise during 20 min. 493 mg (2.20 mmol) 3-chloro-perbenzoic acid (77% peracid) dissolved in 20 ml ethyl acetate. After 1 hour stirring at −30° C. the mixture was allowed to warm up over night, stirred another 48 hours at room temperature, diluted with dichloromethane, washed with sodium bicarbonate solution, then with water, dried and evaporated. Elution from silica with ethyl acetate (1–10% methanol gradient) gave as the second fraction 199 mg (27%) title compound as white solid.

MS: M=501.2 (ESI+). $^1$H-NMR (400 MHz, D$_6$-DMSO): δ=2.30 (s, 3H, CH$_3$), 3.29 (quintet, 1H, CH$_2$—CH2-N), 3.42 (quintet, 1H, CH$_2$—CH2-N), 4.01 (d, 1H, CH$_2$—Ph), 4.15 (d, 1H, CH$_2$—Ph), 4.82 (quintet, 2H, CH$_2$-triazole), 5.01 (s, 2H, OCH$_2$-oxazole), 6.87 (d, 1H, 5-H, OPh), 6.91 (s, 1H, 3-H, OPh), 7.17 (d, 1H, 6-H, OPh), 7.25 (d, 1H, =CH), 7.36 (d, 1H, ClPh), 7.51 (d, 1H, =CH), 7.54 (m, 1H, ClPh), 7.75 (s, 1H, triazole), 7.95 (t, 1H, ClPh), 8.18 (s, 1H, triazole), 8.23 (s, 1H, 5-H-oxazole).

Example 19

1-[2-(4-{2-[(E)-2-(4-Chloro-2-fluoro-phenyl)-vinyl]-oxazol-4-ylmethoxy}-2-methyl-phenylmethanesulfonyl)-ethyl]-1H-[1,2,3]triazole The first fraction from the chromatography of example 18 consisted of 163 mg (22%) title compound as white solid.

MS: M=517.3 (ESI+). $^1$H-NMR (400 MHz, D$_6$-DMSO): δ=2.34 (s, 3H, CH$_3$), 3.82 (t, 2H, CH$_2$—CH2-N), 4.43 (d, H, CH$_2$—Ph), 4.86 (t, 2H, CH$_2$-triazole), 5.03 (s, 2H, OCH$_2$-oxazole), 6.90 (d, 1H, 5-H, OPh), 6.94 (s, 1H, 3-H, OPh), 7.22 (d, 1H, 6-H, OPh), 7.25 (d, 1H, vinyl-H), 7.36 (d, 1H, Ar—Cl), 7.52 (d, 1H, vinyl-H), 7.54 (m, 1H, Ar—Cl), 7.76 (s, 1H, triazole), 7.95 (t, 1H, Ar—Cl), 8.20 (s, 1H, triazole), 8.24 (s, 1H, 5-H-oxazole).

Example 20

1-[2-(4-{2-[(E)-2-(2-Fluoro-4-trifluoromethyl-phenyl)-vinyl]-oxazol-4-ylmethoxy}-2-methyl-phenyl-methanesulfanyl)-ethyl]-1H-[1,2,3]triazole A solution of 500 mg (2.01 mmol) 3-methyl-4-(2-[1,2,3]triazol-1-yl-ethanesulfanylmethyl)-phenol in 16 ml N,N-dimethylformamide was treated at 0° C. with 61 mg (2.4 mmol) sodium hydride and stirred at room temperature for 30 min., then 614 mg (2.01 mmol) 4-chloromethyl-2-[2-(2-fluoro-4-trifluoromethyl-phenyl)-vinyl]-oxazole were added and stirring continued for 12 hours. After addition of 35 ml water, the precipitate was isolated, washed thoroughly with water, water/methanol 1:1, and heptane/ethyl acetate 1:2, and dried in vacuo at 40° C. Yield: 670 mg (64%) 1-[2-(2-methyl-4-{2-[2-(E)-(2-fluoro-4-trifluoromethyl-phenyl)-vinyl]-oxazol-4-ylmethoxy}-benzylsulfanyl)-ethyl]-1H[1,2,3]triazole.

MS: M=519.4(ESI+).

Example 21

1-[2-(4-{2-[(E)-2-(2-Fluoro-4-trifluoromethyl-phenyl)-vinyl]-oxazol-4-ylmethoxy}-2-methyl-phenyl-methanesulfinyl)-ethyl]-1H-[1,2,3]triazole To a solution of 650 mg (1.25 mmol) 1-[2-(2-methyl-4-{2-[2-(E)-(2-fluoro-4-trifluoromethyl-phenyl)-vinyl]-oxazol-4-ylmethoxy}-benzylsulfanyl)-ethyl]-1H[1,2,3]triazole in 35 ml dichloromethane at −30° C. were added dropwise during 20 min. 493 mg (2.20 mmol) 3-chlorobenzenecarboperoxoic acid (77% peracid) dissolved in 20 ml ethyl acetate. After 1 hour stirring at −30° C. the mixture was allowed to warm up over night, stirred another 48 hours at room temperature, diluted with dichloromethane, washed with sodium bicarbonate solution, then with water, dried and evaporated. Elution from silica with ethyl acetate (1–10% methanol gradient) furnished as the second fraction 310 mg (46%) title compound as white solid.

MS: M=535.4 (ESI+). $^1$H-NMR (400 MHz, D$_6$-DMSO): δ=2.30 (s, 3H, CH$_3$), 3.28 (dt, 1H, C$\underline{H}_2$—CH2-N), 3.41 (dt, 1H, C$\underline{H}_2$—CH2-N), 4.02 (d, 1H, CH$_2$—Ph), 4.15 (d, 1H, CH$_2$—Ph), 4.81 (m, 2H, CH$_2$-triazole), 5.03 (s, 2H, OCH$_2$-oxazole), 6.88 (d, 1H, 5-H, OPh), 6.92 (s, 1H, 3-H, OPh), 7.17 (d, 1H, 6-H, OPh), 7.39 (d, 1H, =CH), 7.60 (d, 1H, =CH), 7.64 (d, 1H, FPh), 7.75 (s, 1H, triazole), 7.95 (d, 1H, FPh), 8.18 (s, 1H, triazole), 8.16 (m, 1H, FPh), 8.27 (s, 1H, 5-H-oxazole).

Example 22

1-[2-(4-{2-[(E)-2-(2-Fluoro-4-trifluoromethyl-phenyl)-vinyl]-oxazol-4-ylmethoxy}-2-methyl-phenyl-methanesulfonyl)-ethyl]-1H-[1,2,3]triazole The first fraction from the chromatography of example 21 consisted of 207 mg (30%) title compound as white solid.

MS: M=551.3 (ESI+). $^1$H-NMR (400 MHz, D$_6$-DMSO): δ=2.34 (s, 3H, CH$_3$), 3.83 (t, 2H, C$\underline{H}_2$—CH2-N), 4.43 (d, H, CH$_2$—Ph), 4.86 (t, 2H, CH$_2$-triazole), 5.04 (s, 2H, OCH$_2$-oxazole), 6.89 (d, 1H, 5-H, OPh), 6.94 (s, 1H, 3-H, OPh), 7.22 (d, 1H, 6-H, OPh), 7.39 (d, 1H, vinyl-H), 7.60 (d, 1H, vinyl-H), 7.63 (d, 1H, Ar—CF$_3$), 7.76 (s, 1H, triazole), 7.78 (d, 1H, Ar—CF$_3$), 8.14 (t, 1H, Ar—CF$_3$), 8.20 (s, 1H, triazole), 8.28 (s, 1H, 5-H-oxazole).

Unless stated to the contrary, all compounds in the examples were prepared and characterized as described. All ranges recited herein encompass all combinations and subcombinations included within that range limit. All patents and publications cited herein are hereby incorporated by reference in their entirety.

What is claimed is:

1. Compounds of formula I or pharmaceutically acceptable salts or esters thereof wherein formula I is:

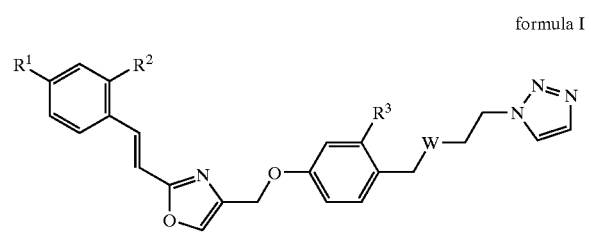

formula I wherein:
(a) R$^1$ is selected from the group consisting of:
  (1) halogenated alkoxy;
  (2) halogenated alkylsulfanyl;
  (3) halogenated alkyl; and
  (4) halogen;
(b) R$^2$ is selected from the group consisting of:
  (1) hydrogen; and
  (2) halogen;
(c) R$^3$ is selected from the group consisting of:
  (1) hydrogen; and
  (2) alkyl; and
(d) W is selected from the group consisting of:
  (1) —S—;
  (2) —S(O)—; and
  (3) —S(O)$_2$—.

2. The compounds according to claim 1, wherein R$^3$ is hydrogen.

3. The compounds according to claim 1, wherein R$^3$ is alkyl.

4. The compounds according to claim 1, wherein R$^1$ is halogenated alkoxy or halogenated alkylsulfanyl.

5. The compounds according to claim 1, wherein:
(a) R$^1$ is selected from the group consisting of:
  (1) halogenated alkoxy; and
  (2) halogenated alkylsulfanyl; and
(b) R$^2$ is hydrogen.

6. A compound according to claim 5 selected from the group consisting of:
(a) 1-[2-(4-{2-[2-(4-Trifluoromethoxy-phenyl)-vinyl]-oxazol-4-ylmethoxy}-benzylsulfanyl)-ethyl]-1H-[1,2,3]triazole;
(b) 1-[2-(4-{2-[2-(4-Trifluoromethoxy-phenyl)-vinyl]-oxazol-4-ylmethoxy}-phenylmethanesulfonyl)-ethyl]-1H-[1,2,3]triazole;
(c) 1-[2-(4-{2-[2-(4-Trifluoromethylsulfanyl-phenyl)-vinyl]-oxazol-4-ylmethoxy}-phenylmethanesulfinyl)-ethyl]-1H-[1,2,3]triazole;
(d) 1-[2-(4-{2-[2-(4-Difluoromethoxy-phenyl)-vinyl]-oxazol-4-ylmethoxy}-phenylmethanesulfinyl)-ethyl]-1H-[1,2,3]triazole;
(e) 1-[2-(4-{2-[2-(4-Trifluoromethoxy-phenyl)-vinyl]-oxazol-4-ylmethoxy}-phenyl-methanesulfinyl)-ethyl]-1H-[1,2,3]triazole;
(f) 1-[2-(2-Methyl-4-{2-[(E)-2-(4-trifluoromethoxy-phenyl)-vinyl]-oxazol-4-ylmethoxy}-phenylmethanesulfanyl)-ethyl]-1H-[1,2,3]triazole;
(g) 1-[2-(2-Methyl-4-{2-[(E)-2-(4-trifluoromethoxy-phenyl)-vinyl]-oxazol-4-ylmethoxy}-phenylmethanesulfinyl)-ethyl]-1H-[1,2,3]triazole; and
(h) 1-[2-(2-Methyl-4-{2-[(E)-2-(4-trifluoromethoxy-phenyl)-vinyl]-oxazol-4-ylmethoxy}-phenylmethanesulfonyl)-ethyl]-1H-[1,2,3]triazole.

7. The compounds according to claim 1, wherein:
(a) R$^1$ is halogenated alkyl or halogen; and
(b) R$^2$ is hydrogen or fluorine.

8. The compounds according to claim 1, wherein R$^1$ is halogenated alkyl.

9. A compound according to claim 8 selected from the group consisting of:
(a) 1-[2-(4-{2-[2-(2-Fluoro-4-trifluoromethyl-phenyl)-vinyl]-oxazol-4-ylmethoxy}-benzylsulfanyl)-ethyl]-1H-[1,2,3]triazole;
(b) 1-[2-(4-{2-[2-(2-Fluoro-4-trifluoromethyl-phenyl)-vinyl]-oxazol-4-ylmethoxy}-phenylmethanesulfinyl)-ethyl]-1H-[1,2,3]triazole;
(c) 1-[2-(4-{2-[2-(2-Fluoro-4-trifluoromethyl-phenyl)-vinyl]-oxazol-4-ylmethoxy}-phenylmethanesulfonyl)-ethyl]-1H-[1,2,3]triazole;
(d) 1-[2-(4-{2-[(E)-2-(2-Fluoro-4-trifluoromethyl-phenyl)-vinyl]-oxazol-4-ylmethoxy}-2-methyl-phenylmethanesulfanyl)-ethyl]-1H-[1,2,3]triazole;
(e) 1-[2-(4-{2-[(E)-2-(2-Fluoro-4-trifluoromethyl-phenyl)-vinyl]-oxazol-4-ylmethoxy}-2-methyl-phenylmethanesulfinyl)-ethyl]-1H-[1,2,3]triazole; and (f) 1-[2-(4-{2-[(E)-2-(2-Fluoro-4-trifluoromethyl-phenyl)-vinyl]-oxazol-4-ylmethoxy}-2-methyl-phenylmethanesulfonyl)-ethyl]-1H-[1,2,3]triazole.

10. The compounds according to claim 1, wherein $R^1$ is halogen.

11. A compound according to claim 10 selected from the group consisting of:

(a) 1-[2-(4-{2-[2-(4-Chloro-phenyl)-vinyl]-oxazol-4-ylmethoxy}-benzylsulfanyl)-ethyl]-1H-[1,2,3]triazole;

(b) 1-[2-(4-{2-[2-(4-Chloro-2-fluoro-phenyl)-vinyl]-oxazol-4-ylmethoxy}-benzylsulfanyl)-ethyl]-1H-[1,2,3]triazole;

(c) 1-[2-(4-{2-[2-(4-Chloro-2-fluoro-phenyl)-vinyl]-oxazol-4-ylmethoxy}-phenylmethanesulfinyl)-ethyl]-1H-[1,2,3]triazole;

(d) 1-[2-(4-{2-[2-(4-Chloro-2-fluoro-phenyl)-vinyl]-oxazol-4-ylmethoxy}-phenylmethanesulfonyl)-ethyl]-1H-[1,2,3]triazole;

(e) 1-[2-(4-{2-[(E)-2-(4-Chloro-2-fluoro-phenyl)-vinyl]-oxazol-4-ylmethoxy}-2-methyl-phenylmethanesulfanyl)-ethyl]-1H-[1,2,3]triazole;

(f) 1-[2-(4-{2-[(E)-2-(4-Chloro-2-fluoro-phenyl)-vinyl]-oxazol-4-ylmethoxy}-2-methyl-phenylmethanesulfinyl)-ethyl]-1H-[1,2,3]triazole; and (g) 1-[2-(4-{2-[(E)-2-(4-Chloro-2-fluoro-phenyl)-vinyl]-oxazol-4-ylmethoxy}-2-methyl-phenylmethanesulfonyl)-ethyl]-1H-[1,2,3]triazole.

12. The compounds according to claim 1, wherein W is —S—.

13. The compounds according to claim 1, wherein W is —S(O)—.

14. The compounds according claim 1, wherein W is —S(O)$_2$—.

15. A process for the manufacture of the compounds of claim 1, wherein:

(a) the compound of formula V wherein $R^3$ and W are defined in claim 1:

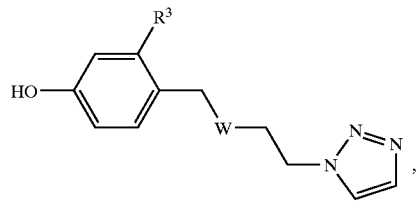

formula V is reacted with a compound of formula IV wherein $R^1$ and $R^2$ are defined in claim 1:

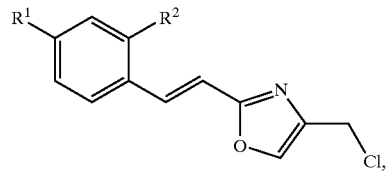

formula IV to give the respective compound of formula I of claim 1;

(b) said compound of formula I is isolated from the reaction mixture, and (c) optionally converted into a pharmaceutically acceptable salt or ester.

16. A pharmaceutical composition comprising a therapeutically effective amount of the compound of claim 1 and a pharmaceutically acceptable carrier.

* * * * *